US010844351B2

(12) United States Patent
Rivolta et al.

(10) Patent No.: US 10,844,351 B2
(45) Date of Patent: Nov. 24, 2020

(54) METHOD FOR PRODUCING OTIC PROGENITORS

(71) Applicant: THE UNIVERSITY OF SHEFFIELD, South Yorkshire (GB)

(72) Inventors: Carlos Marcelo Nicolas Rivolta, South Yorkshire (GB); Darrell Michael Barrott, South Yorkshire (GB)

(73) Assignee: The University of Sheffield, Sheffield (GB)

(*) Notice: Subject to any disclaimer, the term of this patent is extended or adjusted under 35 U.S.C. 154(b) by 22 days.

(21) Appl. No.: 15/562,940

(22) PCT Filed: Mar. 30, 2016

(86) PCT No.: PCT/GB2016/050882
§ 371 (c)(1),
(2) Date: Sep. 29, 2017

(87) PCT Pub. No.: WO2016/156831
PCT Pub. Date: Oct. 6, 2016

(65) Prior Publication Data
US 2018/0087026 A1 Mar. 29, 2018

(30) Foreign Application Priority Data
Mar. 31, 2015 (GB) .................................. 1505605.4

(51) Int. Cl.
C12N 5/0793 (2010.01)
C12N 5/0797 (2010.01)

(52) U.S. Cl.
CPC ........... C12N 5/062 (2013.01); C12N 5/0623 (2013.01)

(58) Field of Classification Search
None
See application file for complete search history.

(56) References Cited

FOREIGN PATENT DOCUMENTS

| WO | 2012103012 | | 8/2012 |
|----|------------|---|--------|
| WO | WO 2012/103012 | * | 8/2012 |
| WO | WO 2012/103102 | * | 8/2012 |
| WO | 2013166488 | | 11/2013 |
| WO | WO 2013/166488 | * | 11/2013 |

OTHER PUBLICATIONS

Chen et al., Nat. Chem. Biol. 5(2): 100-107 (2009).*
International Application No. PCT/GB2016/050882, International Preliminary Report on Patentability dated Oct. 12, 2017, 9 pages.
Boddy et al., "Inner ear progenitor cells can be generated in vitro from human bone marrow mesenchymal stem cells", 2012, Regenerative medicine 7(6): 757-767.

(Continued)

Primary Examiner — Erin M. Bowers
(74) Attorney, Agent, or Firm — Kilpatrick Townsend & Stockton LLP

(57) ABSTRACT

This invention relates to an improved method for generating otic progenitor cells. The invention also relates to uses of such otic progenitor cells, for example as a medicament (e.g. in the treatment of hearing loss, deafness or other auditory disorder associated with loss of inner ear function) and/or in drug screening methods.

19 Claims, 21 Drawing Sheets

(56) References Cited

OTHER PUBLICATIONS

Freter et al., "Progressive restriction of otic fate: the role of FGF and Wnt in resolving inner ear potential", 2008, Development 135(20): 3415-3424.
Lassiter et al., "Signaling mechanisms controlling cranial placode neurogenesis and delamination", 2014, Developmental Biology 389(1): 39-49.
Park et al., "Hindbrain-derived Wnt and Fgf signals cooperate to specify the otic placode in Xenopus", 2008, Developmental biology 324(1): 108-121.
International Application No. PCT/GB2016/050882, International Search Report dated May 17, 2016; 4 pages.
International Application No. PCT/GB2016/050882, International Written Opinion dated May 17, 2016; 4 pages.
Boddy et al., 2013, "Generation of Otic Lineages From Human Induced Pluripotent Stem Cells", Human Gene Therapy, 24(5): A26-A27.
Chen et al., 2012, "Restoration of auditory evoked responses by human ES-cell-derived otic progenitors", Nature 49: 278-284.
GB Application No. 1505605.4, GB Search Report dated Dec. 1, 2015; 3 pages.
Oshima et al., 2010, "Mechanosensitive hair cell-like cells from embryonic and induced pluripotent stem cells", Cell 141: 704-716.
Backhouse et al., "Surgical access to the mammalian cochlea for cell-based therapies", Experimental neurology 214.2 (2008): 193-200.
Blauwkamp et al., "Endogenous Wnt signalling in human embryonic stem cells generates an equilibrium of distinct lineage-specified progenitors", Nature communications 3.1 (2012): 1-10.
Chen et al., "Restoration of Auditory Evoked Responses by human ES-cell-derived otic progenitors", Nature, vol. 490 No. 7419, Sep. 12, 2012, 7 pages.
Corrales et al., "Engraftment and differentiation of embryonic stem cell-derived neural progenitor cells in the cochlear nerve trunk: Growth of processes into the organ of corti", Journal of neurobiology 66.13 (2006): 1489-1500.
Dincer et al., "Specification of functional cranial placode derivatives from human pluripotent stem cells", Cell reports 5.5 (2013): 1387-1402.
Dravid et al., "Defining the role of Wnt/β-catenin signaling in the survival, proliferation, and self-renewal of human embryonic stem cells", Stem cells 23.10 (2005): 1489-1501.
Freyer et al., "Canonical Wnt signaling modulates Tbx1, Eya1, and Six1 expression, restricting neurogenesis in the otic vesicle", Developmental Dynamics 239.6 (2010): 1708-1722.
Hu et al., "Survival and neural differentiation of adult neural stem cells transplanted into the mature inner ear", Experimental cell research 302.1 (2005): 40-47.
Jacques et al., "A dual function for canonical Wnt/β-catenin signaling in the developing mammalian cochlea", Development 139.23 (2012): 4395-4404.
Leung et al., "Differential BMP signaling controls formation and differentiation of multipotent preplacodal ectoderm progenitors from human embryonic stem cells", Developmental biology 379.2 (2013): 208-220.
Livak et al., "Analysis of relative gene expression data using real-time quantitative PCR and the 2—ΔΔCT method", Methods 25.4 (2001): 402-408.
Loh et al., "Efficient endoderm induction from human pluripotent stem cells by logically directing signals controlling lineage bifurcations", Cell stem cell 14.2 (2014): 237-252.
Martinez-Monedero et al., "Differentiation of inner ear stem cells to functional sensory neurons", Developmental neurobiology 68.5 (2008): 669-684.
Meijer et al., "GSK-3-selective inhibitors derived from Tyrian purple indirubins", Chemistry & biology 10.12 (2003): 1255-1266.
Ohyama et al., "Wnt signals mediate a fate decision between otic placode and epidermis", Development 133.5 (2006): 865-875.
Ronaghi et al., "Inner ear hair cell-like cells from human embryonic stem cells", Stem cells and development, vol. 23 No. 11, Jun. 1, 2014, pp. 1275-1284.
Shi et al., "BMP4 induction of sensory neurons from human embryonic stem cells and reinnervation of sensory epithelium", European Journal of Neuroscience 26.11 (2007): 3016-3023.
Sokol, "Maintaining embryonic stem cell pluripotency with Wnt signaling", Development 138.20 (2011): 4341-4350.
Tseng et al., "The GSK-3 inhibitor BIO promotes proliferation in mammalian cardiomyocytes", Chemistry & biology 13.9 (2006): 957-963.
Vendrell et al., "Roles of Wnt8a during formation and patterning of the mouse inner ear", Mechanisms of development 130.2-3 (2013): 160-168.

* cited by examiner

NKA α3 (green)/POU4F1 (red)

FGF

Wnt

β-tubulin III (green)/NF200 (red)

FGF

Wnt

METHOD FOR PRODUCING OTIC PROGENITORS

CROSS REFERENCE TO RELATED APPLICATIONS

This application is a national stage application under 35 U.S.C. § 371 of PCT/GB2016/050882 filed Mar. 30, 2016, which claims priority to GB Application No. 1505605.4 filed Mar. 31, 2015. The disclosures of both of these applications are hereby incorporated by reference herein in their entireties.

This invention relates to an improved method for generating otic progenitor cells. The invention also relates to uses of such otic progenitor cells, for example as a medicament (e.g. in the treatment of hearing loss, deafness or other auditory disorder associated with loss of inner ear function) and/or in drug screening methods.

BACKGROUND

Hearing loss, or deafness, is a condition that affects millions worldwide with a significant impact on the both the health system as a whole and the affected individual's quality of life and integration into society. In the vast majority of cases, the sensory deficit is due to damage or loss of the sensory hair cells and their associated spiral ganglion neurons (SGNs) in the inner ear of the affected individual. Since mammals have lost the ability to regenerate these cells, deafness is irreversible. Of all the forms of deafness, auditory neuropathy is of particular concern. This condition, defined primarily by damage to the SGNs with relative preservation of the hair cells, is responsible for hearing loss in a substantial proportion of patients. Although loss of hair cells can be partially circumvented by a cochlear implant, no routine treatment is available for sensory neuron loss, as poor innervation limits the prospective performance of an implant. Regenerative medicine and the use of sensory cell progenitors produced in vitro offer hope for the treatment of a condition that until now remains without a cure.

Hair-cell-like phenotypes and sensory neurons, with different degrees of functional maturation, have been obtained from mouse stem cell populations (Oshima K, Shin K, Diensthuber M, Peng A W, Ricci A J, Heller S. Mechanosensitive hair cell-like cells from embryonic and induced pluripotent stem cells. Cell., 141(4):704-16 (2010); Martinez-Monedero R, Yi E, Oshima K, Glowatzki E, Edge A S. Differentiation of inner ear stem cells to functional sensory neurons. Dev Neurobiol. 68(5):669-84. (2008)). After transplantation, some cell types have shown successful engraftment but none have shown evidence of functional recovery (Corrales C E, Pan L, Li H, Liberman M C, Heller S, Edge A S. Engraftment and differentiation of embryonic stem cell-derived neural progenitor cells in the cochlear nerve trunk: growth of processes into the organ of *Corti*. J Neurobiol. 66(13):1489-500. (2006)). Although useful for research purposes, these products are therefore unsuitable for a therapeutic application and appropriate cell types of human origin have remained elusive so far. Furthermore, neuroprogenitors isolated from mature human cochleae display limited proliferative and differentiating potential, and hESC-derived neural crest cells may differentiate into sensory neurons by exposure to bone morphogenetic protein (BMP) but lack true otic characteristics (Shi F, Corrales C E, Liberman M C, Edge A S. BMP4 induction of sensory neurons from human embryonic stem cells and reinnervation of sensory epithelium. Eur J Neurosci. 26(11):3016-23. (2007)).

More promising studies have shown that human embryonic stem cells (hESCs) can be used to generate otic progenitors by employing FGF3 and FGF10, molecules involved in otic placode induction, and that these otic progenitors can elicit functional repair on deafened gerbils (Chen et al., 2012). However, the FGF3/10 induction method used is inefficient, yielding approximately 20% of the required cell types only.

A method in which Wnt signalling was manipulated to produce inner ear hair cell-like cells from hESC has also recently been published (Ronaghi et al. 2014). The method begins by forcing aggregation of hESCs into embryoid bodies (EB) in the presence of IGF-1, whilst inhibiting both TGFβ and Wnt. EBs are then plated onto poly-L-ornithine and laminin with bFGF, FGF-19, noggin and R-spondin for 3 days, and at this stage noggin and R-spondin are removed and replaced with BMP4. The Ronaghi method is performed in the presence of Knockout Serum Replacement. The predicted yield of otic progenitors of this method is only around 12.5% of the total cell number.

Although the prior art demonstrate that otic progenitor cells may be successfully generated from hESCs, the methods used are relatively inefficient.

There is a clear need for an improved, reliable method for generating otic progenitor cells, wherein the method has the ability to produce at least one (and ideally both) of the cell types required for sensory replacement (hair-cell like cells and/or auditory (sensory) neurons).

BRIEF SUMMARY OF THE DISCLOSURE

The inventors have investigated the culture conditions necessary for generating otic progenitor cells.

The invention is based on the surprising finding that sequential manipulation of Wnt signalling (initial inhibition, followed by activation) against a backdrop of attenuated FGF signalling during culture of a progenitor cell results in a significant improvement in otic progenitor cell yield (from approximately 20% to near 60%). Accordingly, the invention provides an improved method in which differentiation of progenitor cells from pluripotent stem cells (e.g. hESC) is induced using modified signalling of the otic placode.

The Wnt signalling pathway is known to play a role during development of the ear in vivo. The inventors have manipulated the canonical Wnt signalling pathway in combination with FGF for the purpose of otic progenitor differentiation. An initial period of FGF signalling combined with Wnt inhibition has been found necessary to promote an ectodermal identity in the differentiating human embryonic stem cells, with a concomitant increase in the expression of otic markers. Surprisingly, a subsequent phase of Wnt activation with an attenuated FGF signal has been shown to further expand the proportion of otic progenitors, where the resultant yield of otic progenitors is substantially higher than that shown using previous methods in which FGF signalling is maintained in this second phase at the same level as in the first phase.

Advantageously, the typical otic progenitor yield of the improved method described herein is 50 to 60% (of total cell number).

Advantageously, the method results in two populations of otic progenitor cells (otic epithelial progenitors and otic neural progenitors respectively) that are able to further differentiate in vitro into hair-cell-like cells and auditory neurons.

Importantly, the method may be carried out in a monolayer. Unlike methods that require an initial aggregation step, growing the cells as a monolayer facilitates the manual selection and purification of colonies of the desired cell type.

Advantageously, the method can be performed under serum-free culture conditions that avoid the use of knockout serum replacement (KSR), an undefined serum replacement. Moreover, being able to perform the differentiation in a serum-free, defined system will facilitate adapting the protocol to GMP (Good Manufacturing Practice) standards, free from animal products and suitable for clinical application.

The method therefore facilitates the generation of otic progenitor cells that can be used in a clinical setting, for example in the treatment of hearing loss, deafness, or another auditory disorder associated with loss of inner ear function.

Some of the notable advantages of the method are therefore: (i) simplicity (fewer steps), (ii) increased efficiency in the generation of the desired cell type(s) (iii) use of a monolayer culture system that permits the manual selection of colonies, and (iv) serum-free culture conditions that avoid the use of KSR, an undefined serum replacement.

In a first aspect the invention provides a method of generating otic progenitor cells comprising the sequential steps of:

i) culturing a progenitor cell under conditions sufficient to inhibit Wnt signalling and activate FGF signalling for a first time period sufficient to induce upregulation of one or more otic cell markers;

ii) culturing the progenitor cell of step i) under conditions sufficient to activate Wnt signalling and reduce FGF signalling relative to step i) for a second time period sufficient to maintain upregulated expression of said one or more otic cell markers.

In one embodiment said progenitor cell is a pluripotent stem cell. Preferably said pluripotent stem cell is an embryonic stem cell or an induced pluripotent stem cell.

In one embodiment said otic progenitor cells comprise one or more otic epithelial progenitor cells and/or one or more otic neural progenitor cells.

In one embodiment said one or more otic cell markers is selected from PAX2, PAX8, FOXG1 and SOX2.

In one embodiment said upregulation of one or more otic cell markers is determined by measuring gene expression, for example said gene expression is determined by measuring mRNA and/or protein levels.

In one embodiment said conditions sufficient to inhibit Wnt signalling comprise culturing said progenitor cell in a culture medium comprising one or more Wnt inhibitors. Preferably, said one or more Wnt inhibitors is IWR-1-endo.

In one embodiment said conditions sufficient to activate FGF signalling comprise culturing said progenitor cell in a culture medium comprising one or more FGFs. Preferably, said conditions sufficient to reduce FGF signalling comprise culturing said progenitor cell of step ii) in a culture medium comprising one or more FGFs at a lower concentration than said one or more FGFs present in said culture medium of step i). Optionally said one or more FGFs present in the culture medium of step i) are the same as said one or more FGFs present in the culture medium of step ii). Optionally, said one or more FGFs is selected from FGF3 and FGF10.

In one embodiment said progenitor cell is cultured as a monolayer.

In one embodiment said progenitor cell is cultured in serum free conditions.

In one embodiment inhibition of Wnt signalling occurs prior to otic progenitor cell differentiation.

In one embodiment said first time period is at least 24, 48, 72, 96, 120, 144, 168, 192, 216, 240, 264 or 288 hours. Preferably said first time period is at least 144 hours.

In one embodiment said second time period is at least 24, 48, 72, 96, 120, 144, 168, or 192 hours. Preferably said second time period is at least 96 hours.

In one embodiment the method further comprises a step iii) comprising differentiating said otic progenitor cells into hair-cell-like cells.

In one embodiment the method further comprises a step iii) comprising differentiating said otic progenitor cells into auditory or sensory neurons.

In a further aspect the invention provides an otic progenitor cell obtained by the method of the invention.

In a further aspect the invention provides an otic progenitor cell according to the invention for use as a medicament.

In a further aspect the invention provides an otic progenitor cell according the invention for use in the treatment of a hearing loss, deafness, or other auditory disorder associated with loss of inner ear function.

In a further aspect the invention provides an otic progenitor cell according to claim the invention for use in drug screening.

BRIEF DESCRIPTION OF THE DRAWINGS

Embodiments of the invention are further described hereinafter with reference to the accompanying drawings:

FIG. 16 shows the differentiation potential into sensory neurons of otic neuroprogenitors generated by the standard FGF protocol or modified protocol 3.

DETAILED DESCRIPTION

Figure 1:
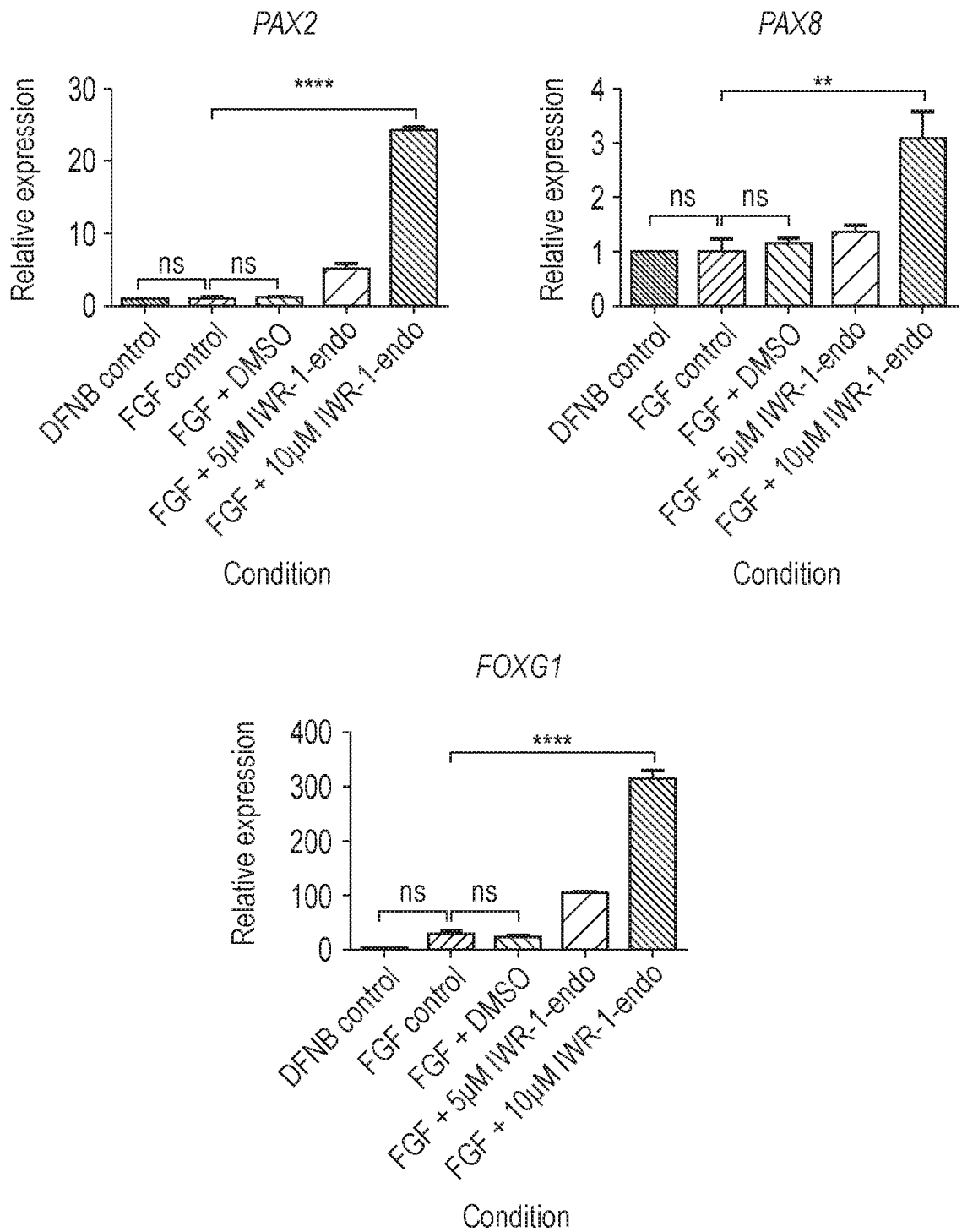
FIG. 1 shows the dose response of IWR-1-endo, present throughout the 12 day protocol, on the gene expression of PAX2, PAX8 and FOXG1 in the H14S9 hES cell line, seeded at $8 \times 10^3$ cells/cm$^2$. Compound was reconstituted in the vehicle DMSO and a vehicle only control was also included. Bar charts denote mean and standard deviation of gene expression relative to that of the DFNB control condition (n=2 independent experiments). Statistical significance was determined by one way ANOVA with Bonferroni's multiple comparison post-test. ns=no significant difference. *$P<0.05$, $P<0.01$, **$P<0.0001$.
Figure 2A:
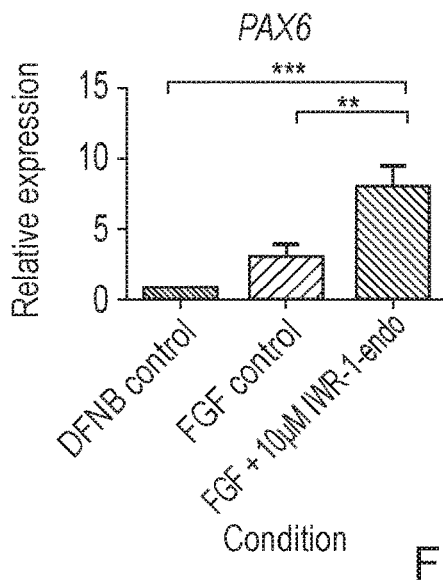
FIG. 2 shows gene expression of markers associated with ectoderm (A), mesoderm (B) and endoderm (C) lineage differentiation following a 12 day differentiation protocol with H14S9 hES cells, seeded at $8 \times 10^3$ cells/cm$^2$. Compound was present throughout the protocol from the initial day of seeding. Gene expression is presented as relative to that of the DFNB baseline control. Bar charts denote mean and standard deviation of gene expression relative to that of the DFNB control condition (n=3 independent experiments). Statistical significance was determined by one way ANOVA with Tukey's multiple comparison post-test. ns=no significant difference. *$P<0.05$, $P<0.01$, *$P<0.001$, ****$P<0.0001$.
Figure 2A:
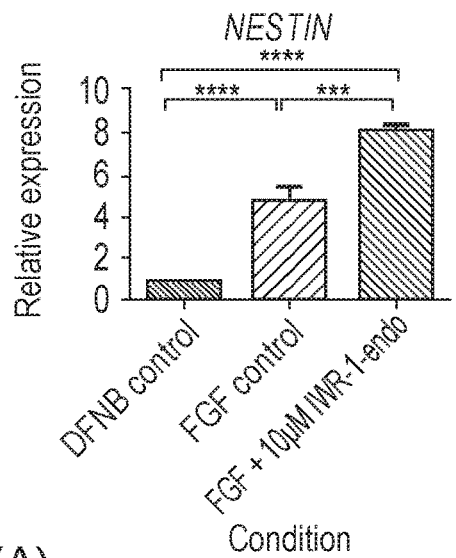
Figure 2B:
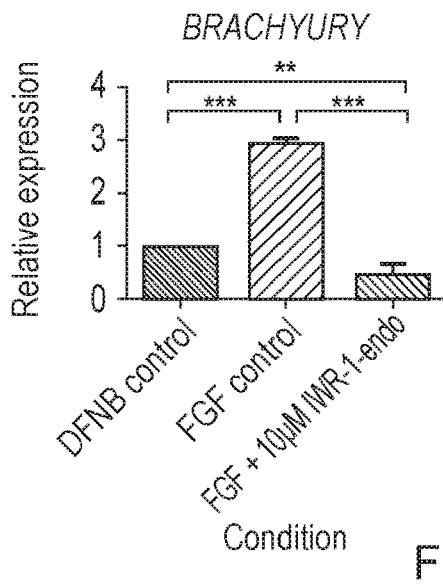
Figure 2B:
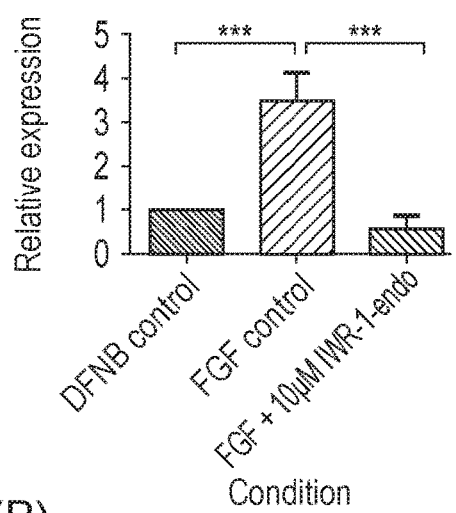
Figure 2C:
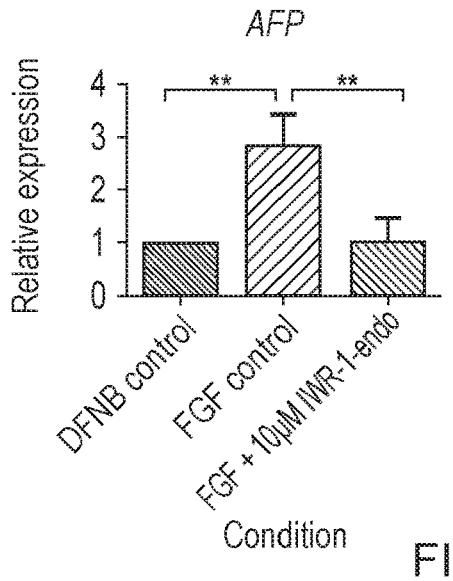
Figure 2C:
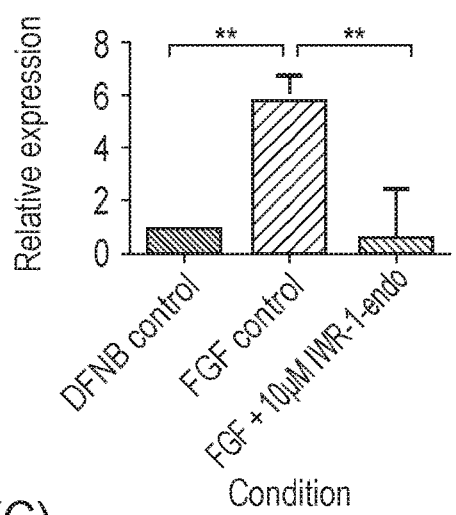

The invention is based on the surprising finding that sequential manipulation of Wnt signalling (initial inhibition, followed by activation) against a backdrop of attenuated FGF signalling during culture of a progenitor cell results in a significant improvement in otic progenitor cell yield (from approximately 20% to near 60%). Accordingly, the invention provides an improved method in which differentiation of progenitor cells from pluripotent stem cells (e.g. hESC) is induced using modified signalling of the otic placode.

Advantageously, the method results in two populations of otic progenitor cells (known herein as "otic epithelial progenitors" (OEPs) and "otic neural progenitors" (ONPs)) that are able to further differentiate in vitro into hair-cell-like cells and auditory neurons (also called sensory neurons herein) that display expected electrophysiological properties respectively.

The method therefore facilitates the generation of otic progenitor cells that can be used in a clinical setting, for example in the treatment of hearing loss, deafness, or another auditory disorder associated with loss of inner ear function.

Cells

The method comprises culturing a progenitor cell under specified conditions that result in the generation of otic progenitor cell(s).

As used herein, the terms "progenitor cell" and "stem cell" are used interchangeably to refer to a biological cell that is capable of self-renewing and differentiating into a more mature cell. The term "progenitor cell" encompasses, but is not limited to, pluripotent stem cells such as embryonic stem cells (e.g. hESC) or induced pluripotent stem cells.

The method differentiates progenitor cell(s) into one or more otic progenitor cells. As used herein, an "otic progenitor cell" refers to an immature cell having the capacity to self-renew and to differentiate into more mature cell, but is also committed to a certain cell lineage (e.g., otic progenitor cells are committed to the otic lineage). The term "otic progenitor cell" encompasses, but is not limited to, otic epithelial progenitor cells and/or otic neural progenitor cells.

The method may generate a mixed population of cells, comprising one or more otic progenitor cells and one or more other (non-otic progenitor) cells. The one or more otic progenitor cells may also comprise a mixed population of, for example, one or more otic epithelial progenitor cells and/or one or more otic neural progenitor cells.

Advantageously, the method results in a mixed population of otic progenitor cells comprising two populations of otic progenitor cells (known herein as "otic epithelial progenitors" (OEPs) and "otic neural progenitors" (ONPs)) that are able to further differentiate in vitro into hair-cell-like cells and auditory neurons (or sensory neurons) that display expected electrophysiological properties respectively.

The method uses sequential manipulation of Wnt signalling (initial inhibition, followed by activation) against a backdrop of attenuated FGF signalling during culture of a progenitor cell to significantly improve otic progenitor cell yield compared to methods known in the art (from approximately 20% to near 60% of total cell number).

As used herein, "otic progenitor cell yield" refers to the number of otic progenitor cells generated by the method. The yield may be calculated by the number of otic progenitor cells as a percentage of the total number of cells in the culture (or representative sample thereof). The otic progenitor yield may be at least 5%, 10%, 15%, 20%, 25%, 30%, 35%, 40%, 45%, 50%, 55%, 60%, 65%, 70%, 75% etc of the total cell number.

The method may be biased towards the generation of a particular type of otic progenitor cell (for example an otic epithelial progenitor cell or an otic neural progenitor cell). By way of example, the total number of otic epithelial progenitor cells may be more than the total number of otic neural progenitor cells (or vice versa). Alternatively, the total number of otic epithelial progenitor cells may be the same (or approximately the same) as the total number of otic neural progenitor cells.

Culture

The progenitor cell(s) are cultured under specified conditions to generate the otic progenitor cell(s).

As used herein, "culture" and "cell culture" are used interchangeably and refer to the process whereby cells, preferably progenitor cells, are grown (e.g. divide) under controlled conditions, preferably in vitro or ex vivo. Preferably, the cells are cultured in culture medium.

As used herein the terms "medium", "culture medium", "culture media" and "media" are used interchangeably. Preferably, the cells are cultured in a defined culture media containing the minimum essential elements necessary to maintain the growth of (mammalian) progenitor cells, wherein the components of the media are both known and controlled. Such defined minimum essential media for progenitor cell culture are known in the art.

As used herein, "standard FGF differentiation medium" and "standard FGF medium" are used interchangeably to refer to the FGF medium used in Chen et al., 2012 (i.e. medium comprising a 1:1 mixture of Dulbecco's Modified Eagle's Medium (DMEM, high glucose) and F12, supplemented with 1×N2 and 1×B27, FGF3 (50 ng ml−1) and FGF10 (50 ng ml−1).

As used herein, "standard FGF differentiation protocol", "standard FGF protocol" and "standard FGF condition" are used interchangeably to refer to the FGF differentiation protocol used in Chen et al., 2012, wherein cells are plated on laminin-coated dishes in a 1:1 mixture of Dulbecco's Modified Eagle's Medium (DMEM, high glucose) and F12, supplemented with 1×N2 and 1×B27, FGF3 (50 ng ml−1) and FGF10 (50 ng ml−1).

Chemically defined culture media for (mammalian) cell culture have been extensively developed and published over the last several decades. All components of defined media are well characterized. Defined media typically consist of roughly fifty chemical entities at known concentrations in water. The chemical components of the media fall into four broad categories: amino acids, vitamins, inorganic salts, trace elements.

The trace elements consist of a variety of inorganic salts included at micromolar or lower levels. The four most commonly included trace elements present in almost all defined media are iron, zinc, selenium and copper. Iron (ferrous or ferric salts) and zinc are typically added in micromolar concentrations, while the others are usually at nanomolar concentrations. The numerous less common trace elements are usually added at nanomolar concentrations.

Defined culture media comprising minimum essential elements necessary to maintain the growth of mammalian cells are well known in the art and include, by way of example only Minimum Essential Medium Eagle, Minimum Essential Medium Dulbecco, ADC-I, LPM (Bovine Serum Albumin-free), FIO(HAM), F12 (HAM), DCCMI, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M 199 (M 199H— with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' E, Williams' G, Neuman & Tytell, Higuchi, MCDB 301, MCDB 202, MCDB 501, MCDB 401, MCDB 411 and MDBC 153

The defined culture media may be supplemented with additional supplementary components at the beginning of the culture process or at a time or times subsequent to the beginning of the culture process. In certain embodiments, supplementary components may be added to the initial cell culture. In certain embodiments, supplementary components may be added after the beginning of the cell culture.

Additionally or alternatively, the defined culture media may also be supplemented with one or more carbon sources, nitrogen sources, inorganic salts, vitamins and/or trace elements, or any mixture and/or combination thereof.

Additionally or alternatively, the defined culture media may also be supplemented with one or more growth factors.

As used herein, the terms "growth factor" or "growth factors" refer to any substance capable of maintaining or stimulating cellular growth, proliferation and/or cellular differentiation, including cytokines, steroids and hormones. Exemplary growth factors include, but are not limited to IGFs, such as IGF-I and IGF-II, VEGF, PDGF, EGF, fibroblast growth factor, bFGF, osteopontin, thrombospondin-1, tenascin-C, PAI-1, plasminogen, fibrinogen, fibrin, transferrin, Adenine, Adrenomedullin, Angiopoietin, Autocrine motility factor, Bone morphogenetic proteins, Brain-derived neurotrophic factor, Epidermal growth factor, Erythropoietin, Fibroblast growth factor, Glial cell line-derived neurotrophic factor, Granulocyte colony-stimulating factor, Granulocyte macrophage colony-stimulating factor, Growth differentiation factor-9, Hepatocyte growth factor, Hepatoma-derived growth factor, Hydrocortisone, Insulin, Insulin-like growth factor, L-glutamine, Migration-stimulating factor, Myostatin, Nerve growth factor and other neurotrophins, Platelet-derived growth factor, Transferrin, Thrombopoietin, Transforming growth factor alpha, Transforming growth factor beta, Tri-iodothryonine, Tumor necrosis factor-alpha, Vascular endothelial growth factor, Wnt Signaling Pathway, placental growth factor, Foetal Bovine Somatotrophin, IL-1, IL-2, IL-3, IL-4, IL-5, IL-6, IL-7, or any biological equivalent, derivative or combination thereof.

Additionally or alternatively, the defined culture media may also be supplemented with one or more antibiotics. As used herein, the term "antibiotic" or "antibiotics" refers to any natural or synthetic substance that inhibits the growth of or destroys microorganisms. For example, the antibiotic may inhibit cell wall synthesis, protein synthesis, nucleic acid synthesis, or alter cell membrane function. Examples of antibiotics include amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol and zithromycin, or any mixture or combination thereof. Preferably, the media is supplemented with penicillin and/or streptomycin. Preferably the antibiotic supplemented culture medium comprises from about 0.5 to about 1.5% (v/v) antibiotic, more preferably about 1% (v/v) antibiotic.

The progenitor cell(s) may be cultured in serum free conditions. As used herein "serum free conditions" are conditions in which serum is omitted (e.g. from the culture medium) such that e.g. the culture medium does not comprise (i.e. is essentially free from or not supplemented with) serum. Optionally, the conditions of step (i) and/or step (ii) are serum free.

By way of example only (and not for the purposes of limitation), the method of the invention may be performed using a base medium such as DFNB to which the appropriate supplements (e.g. inhibitors, agonists and/or FGF(s)) are added. Within the context of DFNB, "D" refers to DMEM, "F" refers to F12, "N" refers to N2 and "B" refers to B27, all of which are commercially available and well known. An alternative base medium that may also be used in DFB (i.e. DFNB without N2). It is noted that any appropriate base medium may be used, a number of which will be readily identifiable by a person of skill in the art.

The progenitor cells may be cultured as a monolayer. As used herein, a "monolayer" refers to a layer of cells in which no cell is growing on top of another, but all are growing side by side and often touching each other on the same growth surface.

In step (i) of the method, the progenitor cell is cultured under conditions sufficient to inhibit Wnt signalling and activate FGF signalling for a first time period sufficient to induce upregulation of one or more otic cell markers.

As used herein, "conditions sufficient to inhibit Wnt signalling" refers to any conditions that partially or completely reduce Wnt signalling in the progenitor cell of step (i) compared to the level of Wnt signalling in an equivalent progenitor cell that is not subjected to such conditions ("control"). Inhibition (i.e. reduction in Wnt signalling) may be at least 10%, 20%, 30%, 40%, 50%, 60%, 70%, 80%, 90%, 95%, 99% or 100% compared to control. Optionally, the conditions are such that there is no measurable Wnt signalling in the progenitor cell of step (i) (e.g. Wnt signalling in completely inhibited e.g. there is a 100% reduction compared to control). Methods for measuring Wnt signalling are well known to a person of skill in the art.

Conditions that are sufficient to inhibit Wnt signalling include culturing the progenitor cell in a culture medium comprising one or more Wnt inhibitors (e.g. IWR-1-endo). A person of skill in the art will readily be able to identify suitable Wnt inhibitors and as such any Wnt inhibitor may be used. A person of skill in the art will also readily be able to identify suitable Wnt inhibitor concentrations.

By way of example, the culture of step (i) may be supplemented with one or more Wnt inhibitors, preferably from about 1 to 50 µM of IWR-1-endo, most preferably about 10 µM IWR-1-endo.

Preferably, the inhibition of Wnt signalling occurs prior to (i.e. in advance of) any otic progenitor cell differentiation. By way of example, Wnt inhibition may occur on day 0, 1, 2, 3, or 4 of step (i).

As used herein, "conditions sufficient to activate FGF signalling" refers to any conditions that induce (e.g. increase and/or activate) FGF signalling in the progenitor cell of step (i) compared to the level of FGF signalling in an equivalent progenitor cell that is not subjected to such conditions ("control"). Induction (i.e. increase and/or activation in FGF signalling) may be an at least 10%, 20%, 30%, 40%, 50%, 60%, 70%, 80%, 90%, 95%, 99% or 100% increase in FGF signalling compared to control. Methods for measuring FGF signalling are well known to a person of skill in the art.

Conditions that are sufficient to activate FGF signalling include culturing the progenitor cell in a culture medium comprising one or more FGFs. Suitable FGFs are readily identifiable by a person of skill in the art and include (but are not limited to) FGF3 and FGF10. Other suitable FGFs may include FGF2 (also known as bFGF). A person of skill in the art will also readily be able to identify suitable FGF concentrations.

By way of example, the culture of step (i) may be supplemented with one or more FGFs, such as FGF 3 and/or FGF10. Preferably the culture is supplemented with FGF3 at a concentration of from about 1 to 100 ng/ml, most preferably about 50 ng/ml FGF3. In addition, or alternatively, the culture of step (i) may be supplemented with FGF 10 at a concentration of from about 1 to 100 ng/ml, most preferably about 50 ng/ml FGF 10.

The conditions of step (i) must be sufficient to inhibit Wnt signalling and activate FGF signalling.

The (supplemented) culture medium of step (i) may be refreshed (i.e. removed and replaced with fresh culture medium comprising the same supplements) during the first time period. Additionally or alternatively, the (supplemented) culture medium of step (ii) may be refreshed (i.e. removed and replaced with fresh culture medium comprising the same supplements) during the second time period.

The progenitor cell is cultured in step (i) under the specified conditions for a first time period, where the time period is sufficient to induce upregulation of one or more otic cell markers.

As used herein, a "time period sufficient to induce upregulation of one or more otic cell markers" refers to any period of time that allows for upregulation of one of more otic cell markers. Preferably, the first time period is at least about 24 hours, 48 hours, 72 hours, 96 hours, 120 hours, 144 hours, 168 hours, 192 hours, 216 hours, 240 hours, 264 hours or 288 hours. Preferably, the first time period is at least 144 hours. Preferably, the first time period is between from 144 to 216 hours.

As used herein, "upregulation" refers to an increase in the one or more otic cell markers in the progenitor cell that has been cultured under the conditions of step (i) for a first time period compared to the one or more otic cell markers of an equivalent progenitor cell that has not been cultured under the conditions of step (i) for a first time period ("control"). Upregulation of the one or more otic cell markers may be determined by any suitable means known in the art. As an example, upregulation may be determined by measuring the level of otic cell marker gene expression using known methods such as measuring otic cell marker mRNA and/or protein levels, or measuring otic cell marker activity.

An "increase" in the one or more otic cell markers may be represented by an at least 1%, 2%, 5%, 10%, 15%, 20%, 30%, 40%, 50%, 60%, 70%, 80%, 90%, 95%, 99%, 100% or more rise compared to control. Accordingly, an increase in mRNA and/or protein level may be represented by an at least 1%, 2%, 5%, 10%, 15%, 20%, 30%, 40%, 50%, 60%, 70%, 80%, 90%, 95%, 99%, 100% or more rise in mRNA and/or protein level compared to control.

Any known mRNA detection methods may be used to detect the level of otic cell marker mRNA in a sample.

For example, the level of mRNA corresponding to the otic cell marker nucleic acid molecule in a sample can be determined both by in situ and by in vitro formats. Otic cell marker mRNA may be detected using Southern or Northern blot analysis, polymerase chain reaction or probe arrays. By way of example, a sample may be contacted with a nucleic acid molecule (i.e. a probe, such as a labeled probe) that can hybridize to the mRNA encoded by the otic cell marker nucleic acid molecule. The probe may correspond to, for example, a full-length otic cell marker nucleic acid molecule, or a portion thereof, which hybridizes under stringent conditions to an otic cell marker nucleic acid molecule.

Stringent conditions are known to those skilled in the art and can be found in available references (e.g., Current Protocols in Molecular Biology, John Wiley & Sons, N.Y., 1989, 6.3.1-6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C.

Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C.

The level of an otic cell marker mRNA in a sample may be evaluated with nucleic acid amplification, for example by rtPCR, ligase chain reaction, self-sustained sequence replication, transcriptional amplification or any other nucleic acid amplification method, followed by the detection of the amplified molecules using techniques known in the art.

Any known protein detection methods may be used to detect the level of otic cell marker polypeptide (protein) in a sample.

Generally, protein detection methods comprise contacting an agent that selectively binds to an otic cell marker polypeptide, for example an anti-otic cell marker antibody, with a sample to determine the level of otic cell marker polypeptide in the sample. Preferably, the agent or antibody is labeled, for example with a detectable label. Suitable antibodies may be polyclonal or monoclonal. An antibody fragment such as a Fab or F(ab')2 may be used.

As used herein the term "labeled", refers to direct labeling of the probe or antibody by coupling (i.e., physically linking) a detectable substance to the probe or antibody, as well as indirect labeling of the probe or antibody by reactivity with a detectable substance.

The level of otic cell marker polypeptide in a sample may be determined by techniques known in the art, such as enzyme linked immunosorbent assays (ELISAs), immunoprecipitation, immunofluorescence, enzyme immunoassay (EIA), radioimmunoassay (RIA), and Western blot analysis.

The level of otic cell marker polypeptide in a sample may also be determined by determining the level of otic cell marker polypeptide activity in a sample.

The level or activity of otic cell marker in the sample may be compared with the level or activity of otic cell marker in a control sample or with a predetermined reference level for the otic cell marker.

A control sample may be contacted with a compound or agent capable of detecting an otic cell marker nucleic acid molecule, such as mRNA, or genomic DNA, and comparing the level of the otic cell marker nucleic acid molecule in the control sample with the level of otic cell marker nucleic acid molecule in the sample generated by the method of the invention ("test sample").

Additionally or alternatively, the control sample may be contacted with a compound or agent capable of detecting an otic cell marker polypeptide, and the level of otic cell marker protein in the control sample may be compared with the presence of otic cell marker protein in the test sample.

Alternatively, the reference level may be comprised of an otic cell marker expression level from a reference database, which may be used to generate a pre-determined cut off value.

The measured expression level of the otic cell marker may be normalised. Expression levels are normalized by correcting the absolute expression level of otic cell marker in a sample by comparing its expression to the expression of a reference nucleic acid that is not an otic cell marker, e.g., an mRNA, such as an mRNA that is constitutively expressed. This normalization allows the comparison of the expression level in one sample to another sample, or between samples from different sources. This normalized expression can then optionally be compared to a reference level or control. For example, when measuring the level of otic cell marker in a sample, the level may be expressed as an absolute concentration or, alternatively, it may be normalized against a known ubiquitously expressed cell marker, such as Actin, RPLO or Gapdh.

As used herein, "one or more otic cell markers" refers to at least one, and optionally two or more (e.g. three, four, five etc) otic cell markers. Examples of otic cells markers that may be upregulated in the context of the invention include, but are not limited to PAX2, PAX8, FOXG1 and/or SOX2. Other otic cell markers that are known to the skilled person may also be used. Other examples of otic cell markers include nestin, SIX1 and GATA3. Any suitable combinations of otic cell markers may be used (e.g. PAX2 with at least one, two or all three of PAX8, FOXG1 and SOX2; PAX8 with at least one, two or all three of PAX2, FOXG1 and SOX2; FOXG1 with at least one, two or all three of PAX2, PAX8 and SOX2; SOX2 with at least one, two or all three of PAX2, PAX8 and FOXG1).

The method additionally comprises substituting (i.e. removing and replacing) the culture conditions (e.g. culture medium) of step (i) with the culture conditions (e.g. culture medium) of step (ii) and culturing for a second time period.

Step (ii) of the method comprises the progenitor cell of step (i) being cultured under conditions sufficient to activate Wnt signalling and reduce FGF signalling relative to step (i) for a second time period, wherein the second time period is sufficient to maintain upregulated expression of said one or more otic cell markers.

As used herein, a "time period sufficient to maintain upregulated expression of one or more otic cell markers" refers to any period of time in which the upregulated expression of the one or more otic cell markers observed in step (i) is sustained (i.e. the level of expression of the otic cell marker(s) upregulated in step (i) remains increased compared to the level of expression of the same otic cell marker(s) in an equivalent progenitor cell that has not been cultured under the conditions of step (i) for a first time period ("control")). "Increase" and "upregulation" in the context of otic cell marker expression are defined above and apply equally here.

It is noted that in order for "upregulated expression" of one or more otic cell markers to be maintained in step (ii), the level of otic cell marker expression in step (ii) does not need to be at the same level as that in step (i) (or higher)—it just needs to be maintained at a level that is increased (i.e. upregulated) compared to the level of expression of the same otic cell marker(s) in an equivalent progenitor cell that has not been cultured under the conditions of step (i) for a first time period ("control").

Preferably, the second time period is at least about 24 hours, 48 hours, 72 hours, 96 hours, 120 hours, 144 hours, 168 hours or 192 hours. Preferably, the second time period is at least 96 hours.

As used herein, "conditions sufficient to activate Wnt signalling" refers to any conditions that induce (e.g. increase and/or activate) Wnt signalling in the progenitor cell of step (ii) compared to the level of Wnt signalling in an equivalent progenitor cell that is not subjected to such conditions ("control"). Induction (i.e. increase and/or activation in Wnt signalling) may be an at least 10%, 20%, 30%, 40%, 50%, 60%, 70%, 80%, 90%, 95%, 99% or 100% increase in Wnt signalling compared to control. Methods for measuring Wnt signalling are well known to a person of skill in the art.

Conditions that are sufficient to activate Wnt signalling include culturing the progenitor cell in a culture medium comprising one or more Wnt activators (also called Wnt agonists herein). Suitable Wnt agonists are readily identifiable by a person of skill in the art and include (but are not limited to) BIO (6-bromoindirubin-3'-oxime, Tocris). A person of skill in the art will also readily be able to identify suitable Wnt agonist concentrations.

By way of example, the culture of step (ii) may be supplemented with one or more Wnt agonists, such as BIO (6-bromoindirubin-3'-oxime, Tocris). Preferably the culture is supplemented with BIO (6-bromoindirubin-3'-oxime, Tocris) at a concentration of from about 1-10 µM, most preferably about 2 µM.

As used herein "conditions sufficient to reduce FGF signalling relative to step (i)" refers to any conditions that partially or completely reduce FGF signalling in the progenitor cell of step (ii) compared to the level of FGF signalling observed in the equivalent progenitor cell of step (i). The reduction in FGF signalling may be at least 1%, 5%, 10%, 20%, 30%, 40%, 50%, 60%, 70%, 80%, 90%, 95%, 99% or 100% compared to the FGF signalling observed in step (i). Preferably, the FGF signalling of the progenitor cell in step (ii) is reduced relative to step (i) but is not completely abolished (i.e. the FGF signalling in step (ii) is not completely inhibited e.g. is still measurable). Methods for measuring FGF signalling are well known to a person of skill in the art.

Conditions that are sufficient to reduce FGF signalling relative to step (i) include culturing the progenitor cell in a culture medium comprising less FGF than that used in step (i). Suitable FGFs are readily identifiable by a person of skill in the art and include (but are not limited to) FGF3 and FGF10. A person of skill in the art will also readily be able to identify suitable FGF concentrations.

By way of example, the culture of step (Ii) may be supplemented with one or more FGFs, such as FGF 3 and/or FGF10, wherein the concentration of the one or more FGFs used is less than or equal to 90%, 80%, 70%, 60%, 50%, 40%, 30%, 20%, 10%, 5%, 2%, or 1% of that used in step (i). Preferably the culture of step (ii) is supplemented with FGF3 at a concentration of from about 5-30 ng/ml, most preferably about 25 ng/ml FGF3. In addition, or alternatively, the culture of step (ii) may be supplemented with FGF 10 at a concentration of from about 5-30 ng/ml, most preferably about 25 ng/ml FGF 10.

The method may additionally comprise a step (iii) in which the otic progenitor cells (e.g. otic epithelial progenitors) of step (ii) are (further) differentiated into hair-cell-like cells. Suitable methods for differentiating such otic progenitor cells into hair-cell-like cells are known to a person of skill in the art (see for example Chen et al., 2012). By way of example, the desired progenitor colonies (e.g. otic epithelial progenitors) of step (ii) may be purified using sequential dissociation to yield moderately homogeneous cultures of the desired cell colony type, followed by expansion of the cells e.g. in otic stem cell full media (OSCFM) comprising a 1:1 mixture of high glucose DMEM (4.5 g/l D-Glucose) plus F12, N2 and B27 supplements, 20 ng/ml recombinant human bFGF, 50 ng/ml recombinant human IGF-1 and 20 ng/ml recombinant human EGF. "Hair-cell" culture conditions may then be used to produce differentiated hair-cell-like cells, for example by culturing in a 1:1 mixture of high glucose DMEM (4.5 g/l D-Glucose) plus F12, N2 and B27, supplemented with $10^{-6}$M All-trans Retinoic Acid (Sigma) and 20 ng/ml EGF.

As used herein, "hair-cell-like cell" refers to a cell that simultaneously expresses ATOH1 and BRN3C, or BRN3C and MYO7A.

Alternatively or additionally, the method may additionally comprise a step (iii) in which the otic progenitor cells (e.g. otic neural progenitors) of step (ii) are (further) differentiated into auditory or sensory neurons. Suitable methods for differentiating such otic progenitor cells into auditory or sensory neurons are known to a person of skill in the art (see for example Chen et al., 2012). By way of example, the desired progenitor colonies (e.g. otic neural progenitors) of step (ii) may be purified using sequential dissociation to yield moderately homogeneous cultures of the desired cell colony type, followed by expansion of the cells e.g. in otic stem cell full media (OSCFM) as described above. "Neural cell" culture conditions may then be used to produce differentiated auditory or sensory neurons, for example neuronal differentiation may be triggered using a "standard neuralisation protocol" by dissociating cells with trypsin and plating them at a density of 3-4,000 cells/cm². Cells are then cultured in high glucose DMEM plus F12 nutrient solution, N2 and B27, supplemented with recombinant human bFGF (20 ng/ml) plus Shh-C24II (500 ng/ml) for three days. On the third day, medium is supplemented with 10 ng ml−1 of BDNF and NT3 and Shh-C24II is removed at the fifth day.

As used herein, "auditory or sensory neuron" refers to a cell that simultaneously expresses BRN3A and β-tubulin III, or β-tubulin III and NF200.

Use as a Medicament

The otic progenitor cells produced by the methods described herein may be useful as a medicament (in various therapeutic settings). By way of example, such otic progenitor cells may be useful in the treatment of a hearing loss, deafness or other auditory disorder associated with loss of inner ear function.

As used herein, the phrase "hearing loss" refers to any diminished sensitivity to the sounds normally heard by a non-affected subject. The severity of a hearing loss is categorized according to the increase in volume above the usual level necessary before the listener can detect it. The term "hearing loss" is used herein to refer to all degrees (severities) of hearing loss (from a minor level of hearing loss e.g. less than 1%, 2%, 5%, 10%, 20%, 30%, 40%; a moderate level of hearing loss e.g. less than 45%, 50%, 55%, 60%, 70%, 80%, 90%, 95%, 99%; or total loss of hearing e.g. 100%).

As used herein, "deafness" is defined as a degree of impairment such that a person is unable to understand speech even in the presence of amplification. In profound deafness, even the loudest sounds produced by an audiometer (an instrument used to measure hearing by producing pure tone sounds through a range of frequencies) may not be detected. In total deafness, no sounds at all, regardless of amplification or method of production, are heard. The term "deafness" is used herein to refer to all degrees of deafness (including partial and total/profound deafness).

As used herein, "other auditory disorder associated with loss of inner ear function" includes diseases and disorders that affect the vestibular function.

The otic progenitor cells produced by the methods of the invention may be transplanted into an ear of a subject in need thereof. Transplantation of the cells into the inner ear of a subject can be useful for restoring or improving the ability of the subject to hear, or for decreasing the symptoms of vestibular dysfunction. Inner ear cells derived from progenitor cells according to the methods described herein need not be fully differentiated to be therapeutically useful. A partially differentiated cell that improves any symptom of a hearing loss, deafness, or other auditory disorder associated with loss of inner ear function in a subject is useful for the therapeutic compositions and methods described herein.

The subject is preferably a mammal, for example a primate, preferably a human or alternatively a rodent.

The subject can be deaf or have a hearing loss for any reason or as a result of any type of event. For example, a human can be deaf because of a genetic or congenital defect; for example, a human can have been deaf since birth, or can be deaf or hard-of-hearing as a result of a gradual loss of hearing due to a genetic or congenital defect. In another example, a human can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants. A human can have a hearing disorder that results from aging, or the human can have tinnitus (characterized by ringing in the ears).

The cells can be administered by any suitable method. For example, to restore hearing, inner ear cells generated by a method described herein can be transplanted, such as in the form of a cell suspension or by using a suitable device or scaffold, into the ear by injection, such as into the luminae of the cochlea. See, e.g., the methods described in Corrales et al., J. Neurobiol. 66(13):1489-500 (2006); Backhouse et el, Experimental Neurology 214 (2008) 193-200 and Hu et al., Experimental Cell Research 302:40-47 (2005). Injection can be, for example, through the round window of the ear or through the bony capsule surrounding the cochlea. The cells can be injected through the round window into the auditory nerve trunk in the internal auditory meatus or into the scala tympani. In a preferred embodiment, the cells are administered into or near the sensory epithelium of the subject, e.g., into a fluid (perilymph)-filled space above or below the sensory epithelium or directly into the nerve trunk or the cochlear modiolus (as in Chen et al, 2012).

Use in Drug Screening

Otic progenitors generated in accordance with the invention may be used as platforms for drug screening. For example, the otic progenitors may be used in screens to identify compounds that will a) enhance hair cell differentiation, repair or survival; b) enhance neuronal differentiation, repair or survival; c) prevent damage and/or apoptosis to the hair cells and neurons induced by noise, aging or cytotoxic drugs; and d) induce generation of new hair cells or neurons by phenotypic conversion/transdifferentiation of supporting cells.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Examples

1. Wnt Manipulation in Early Otic Differentiation 1.1 Canonical Wnt Signalling Inhibition in Combination with FGF 3 and FGF 10 Upregulates Otic Marker Gene Expression The roles of the canonical Wnt signalling pathway in controlling lineage specification (endoderm, mesoderm, and ectoderm) during embryogenesis have been fairly well characterised in vivo (Blauwkamp et al., 2012, Loh et al., 2014, Sokol, 2011). The inventors have investigated whether this information could be advantageously used for the generation of otic progenitors in vitro.

A commercially available canonical Wnt inhibitor (Inhibitor of Wnt Response-1-endo, IWR-1-endo, Calbiochem) was tested. IWR-1-endo mode of action is to stabilise Axin2, a component of the β-catenin destruction complex leading to proteasome-mediated proteolysis of phosphorylated β-catenin (Chen et al., 2009).

The effect of the Wnt inhibitors was initially explored in the backdrop of a known differentiation protocol, which includes FGF 3 and FGF 10 supplementation from the outset. Experiments were carried out to determine the effect of canonical Wnt inhibition on the differentiation of otic progenitors in FGF medium (standard concentration of 50 ng/ml for each FGF 3 and FGF 10) and obtain an optimal working concentration. IWR-1-endo was present from day 0 of differentiation (day 0 refers to the initial seeding of the hES cells into differentiation conditions) and were maintained throughout the 12 day protocol. At the end of the differentiation protocol, RNA was extracted and PAX2, PAX8 and FOXG1 gene expression was quantified by real time PCR (QPCR) using SYBR Green (Sigma Aldrich). Delta Cts were calculated against the large ribosomal protein RPLPO housekeeping gene, and Delta Ct values were compared against the levels expressed by cells differentiated in the control DFNB medium (Livak and Schmittgen, 2001). FIG. 1 compares the dose responses of IWR-1-endo and the effect on the gene expression of PAX2, PAX8 and FOXG1 in the H14S9 hES cell line. Dimethyl sulfoxide (DMSO) was the vehicle for all small molecule compounds. A vehicle-only control was added to FGF medium to ascertain the effects of DMSO. It was observed that DMSO added to the standard FGF differentiation medium did not significantly affect expression of any of the otic markers investigated. This provided confidence that the Wnt inhibitor compound was exerting an effect on gene expression, and not the carrier vehicle. 10 μM IWR-1-endo was chosen for future experiments, as this concentration overall led to a more robust and reproducible upregulation of PAX2, PAX8 and FOXG1. The optimal concentration of IWR-1-endo agrees with published findings in human stem cell studies (Chen et al., 2009, Hudson et al., 2012). 20 µM IWR-1-endo was also tested but this concentration caused very high levels of cell death in the cultures.

1.2 Canonical Wnt Inhibition in Combination with FGF 3 and FGF 10 Upregulates Gene Expression of Ectodermal Markers, but Disrupts Gene Expression of Endodermal and Mesodermal Markers The effect of disrupting canonical Wnt signalling with various small molecule inhibitors present throughout the full 12 days of the otic differentiation protocol giving rise to an upregulation of the characteristic otic markers led to the investigation of the expression of genes associated with lineage differentiation. It was anticipated that the standard FGF differentiation protocol used herein would drive the differentiating hES cells towards an ectodermal fate (as the otic placode is ectodermal in origin). The effect on endoderm and mesoderm differentiation in the FGF condition has not been addressed, and the consequence of combining FGF treatment with canonical Wnt signalling manipulation on lineage differentiation has also not been investigated herein.

With the H14S9 hES cell line, 12 day otic differentiation experiments were carried out in control DFNB, FGF, or FGF with 10 µM IWR-1-endo supplemented medium. Gene expression of the three germ layer lineages relative to the baseline DFNB condition were quantified by QPCR. Two gene markers for each germ layer were investigated; PAX6 and NEST/N (ectoderm), BRACHYURY and MEOX1 (mesoderm), and AFP and GATA6 (endoderm) (FIG. 2).

Compared to the DFNB baseline condition, the standard FGF medium used herein led to the upregulation of genes associated with all three germ layers. It was anticipated that the addition of FGF 3 and FGF 10 would induce ectodermal differentiation but would have no effect on mesoderm and endoderm differentiation. This was not the case however. Significant upregulation of the ectoderm genes PAX6 and NEST/N was observed in the FGF condition as expected, yet significant upregulation of mesoderm and endoderm markers was also observed in the FGF condition. When the FGF medium was supplemented with the canonical Wnt inhibitor IWR-1-endo ectodermal differentiation was enhanced further over the FGF condition, particularly PAX6. However, the gene expression of mesoderm and endoderm markers was significantly reduced compared to the FGF condition. This downregulation effect was seen with the supplementation of all three canonical Wnt inhibitors (especially IWR-1-endo) in FGF medium for BRACHYURY, MEOX1, and GATA6. Only supplementation with IWR-1-endo could cause significant downregulation of AFP however.

Figure 3A:
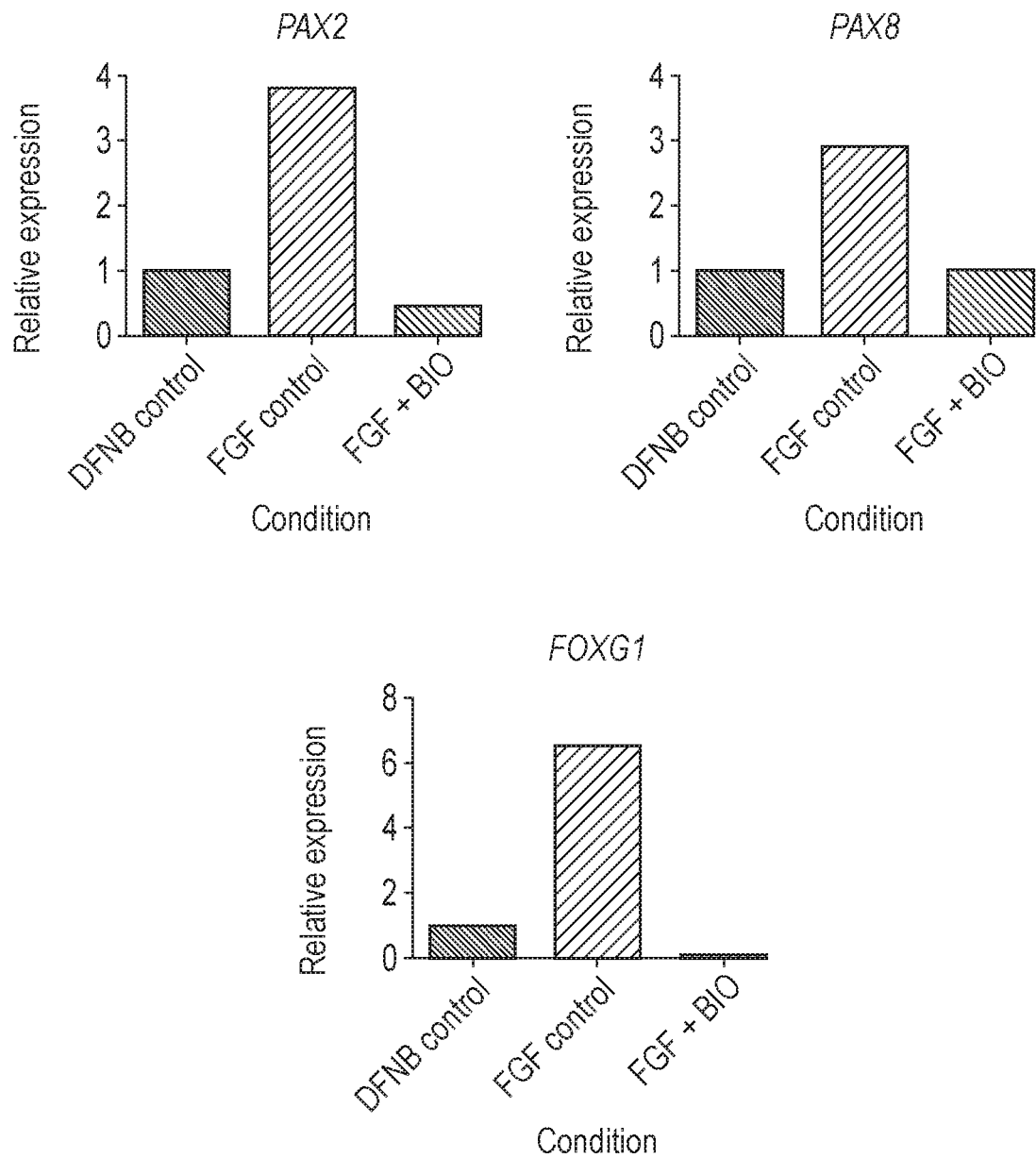
FIG. 3 shows gene expression of otic markers PAX2, PAX8 and FOXG1 (A) and markers of ectoderm (PAX6, NEST/N), mesoderm (BRACHYURY, MEOX1) and endoderm (AFP, GATA6) (B) following a 12 day differentiation protocol with H14S9 hES cells, seeded at $8 \times 10^3$ cells/cm$^2$. BIO was supplemented into FGF medium and maintained throughout. Gene expression is presented as relative to that of the DFNB baseline control. One experiment was carried out and so statistical significance cannot be determined.
Figure 3B:
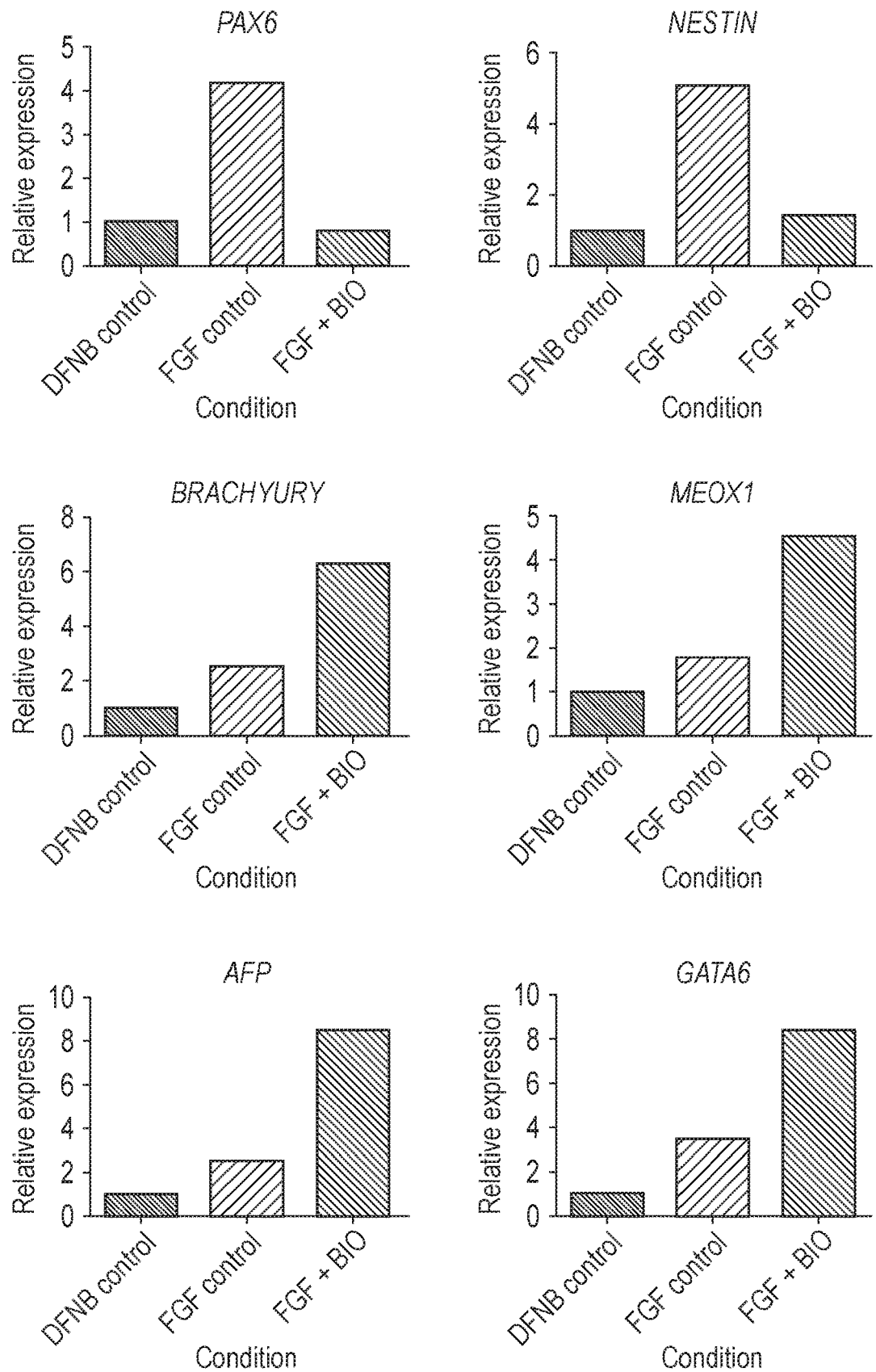

Following a lost-of function/gain-of function paradigm, an experiment was done to determine the effect of activating canonical Wnt signalling throughout the 12 days of otic differentiation. The small molecule compound BIO (6-bromoindirubin-3'-oxime, Tocris) is a potent inhibitor of GSK-3β kinase, a component of the β-catenin degradation complex. Inhibition of GSK-3β kinase activity disrupts the proteolytic breakdown of β-catenin and so Wnt activity is sustained (Meijer et al., 2003). BIO is well established in the literature and has been used to investigate survival and proliferation of hES cells and also lineage differentiation studies (Dravid et al., 2005) (Tseng et al., 2006). BIO was tested at a concentration of 2 µM (as recommended in the literature). FIG. 3 shows the effect on the gene expression of otic markers PAX2, PAX8 and FOXG1 (A), and also markers of ectoderm, mesoderm and endoderm lineage differentiation (B). In contrast to inhibiting canonical Wnt signalling throughout the 12 day protocol, activating canonical Wnt signalling throughout appears to downregulate gene expression of the otic and ectoderm markers, with upregulation of markers of mesoderm and endoderm.

Figure 4:
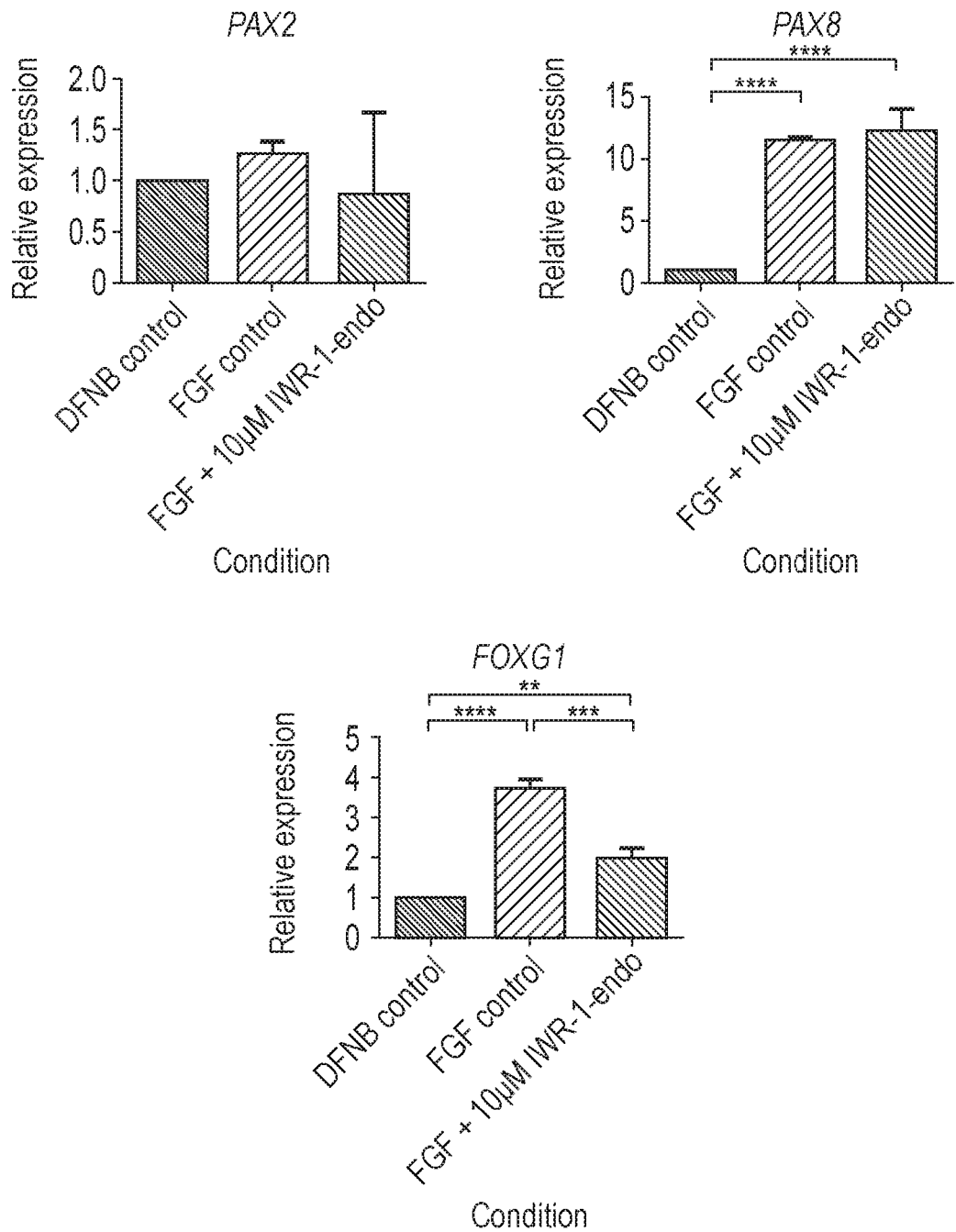
FIG. 4 shows gene expression of otic markers PAX2, PAX8 and FOXG1 following a 12 day differentiation protocol with H14S9 hES cells, seeded at $8 \times 10^3$ cells/cm$^2$. Canonical Wnt inhibitor was supplemented into the media on day 4 and maintained until day 12. Gene expression is presented as relative to that of the DFNB baseline control. Bar charts denote mean and standard deviation of gene expression relative to that of the DFNB control condition (n=3 independent experiments). Statistical significance was determined by one way ANOVA with Tukey's multiple comparison post-test. ns=no significant difference. *P<0.05, P<0.01, **P<0.0001.
Figure 5A:
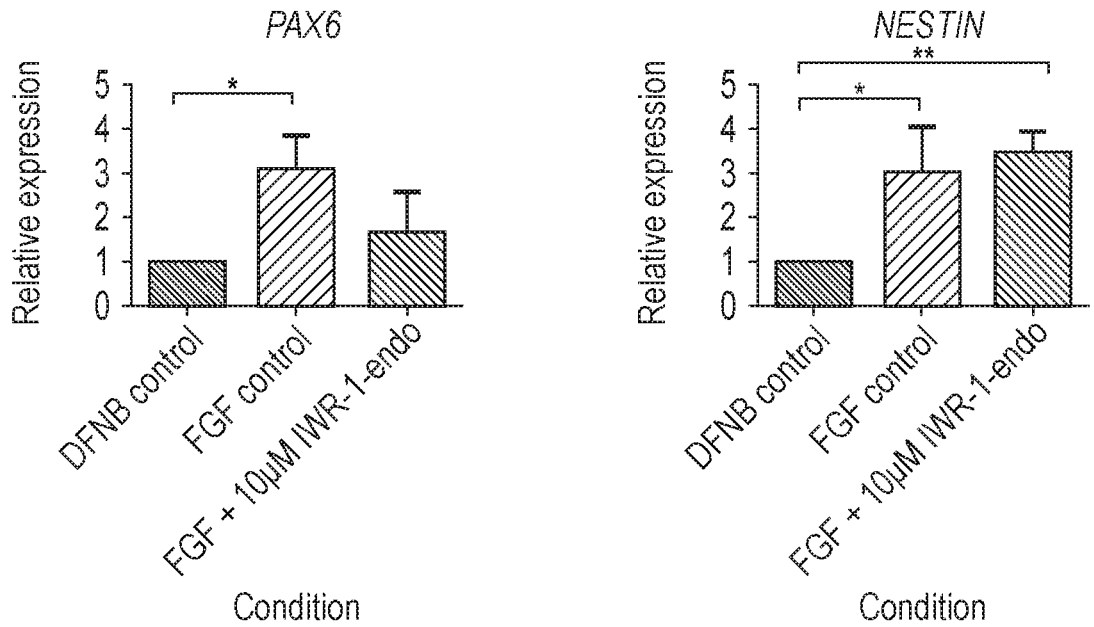
FIG. 5 shows gene expression of markers associated with ectoderm (A), mesoderm (B) and endoderm (C) lineage differentiation following 12 day differentiation with H14S9 hES cells, seeded at $8 \times 10^3$ cells/cm$^2$. Canonical Wnt inhibitor was supplemented into the media from day 4 and maintained throughout to day 12. Gene expression is presented as relative to that of the DFNB baseline control. Bar charts denote mean and standard deviation of gene expression relative to that of the DFNB control condition (n=3 independent experiments). Statistical significance was determined by one way ANOVA with Tukey's multiple comparison post-test. ns=no significant difference. *P<0.05, P<0.01, *P<0.001, ****P<0.0001.
Figure 5B:
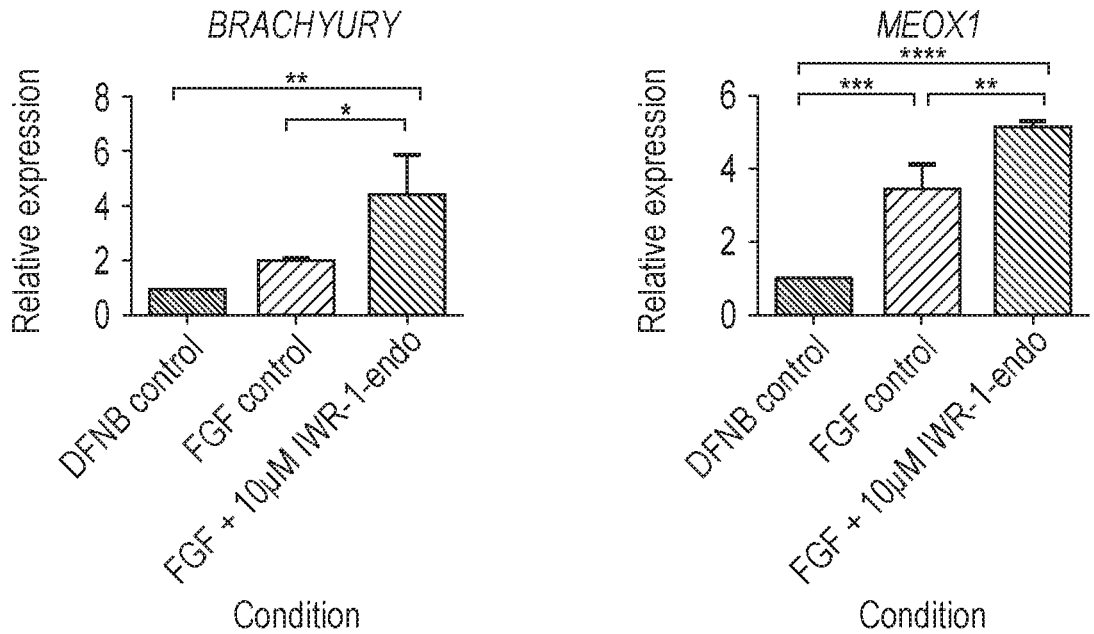
Figure 5C:
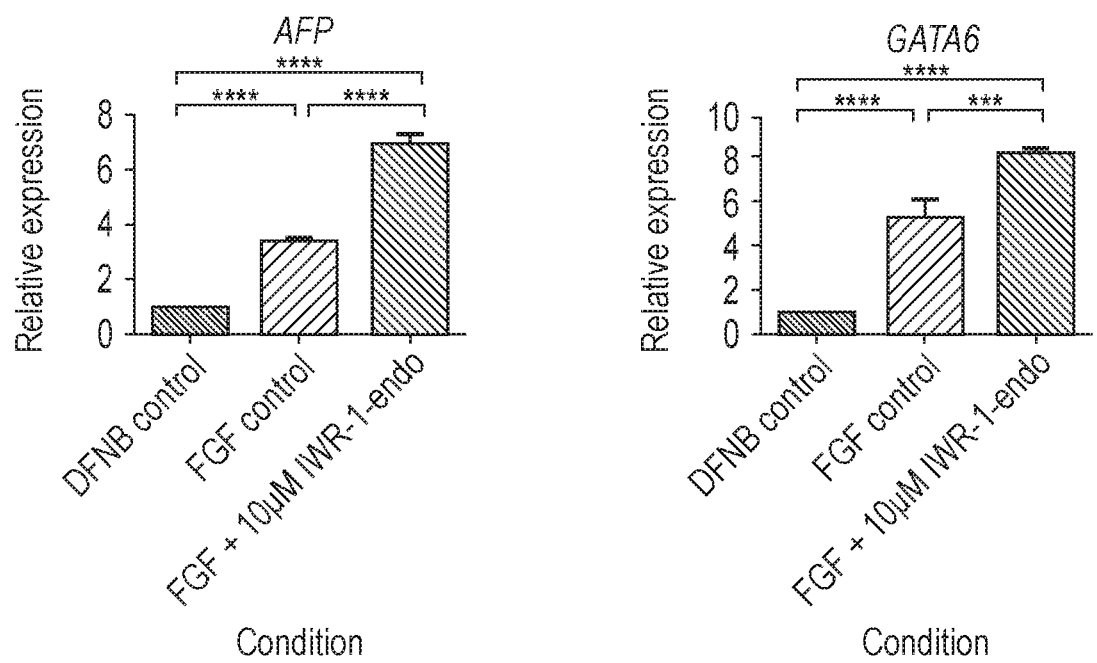

1.3 Timing of Canonical Wnt Inhibition is Critical for Upregulation of Otic Marker Gene Expression Previous experiments have involved supplementing the FGF medium with one of three canonical Wnt inhibitor compounds and maintaining this supplementation throughout the full 12 day protocol, leading to upregulation of the gene expression of the characteristic otic markers. Since timing and sequence of developmental signals is critical to drive a particular process, it was important to determine whether it is necessary for canonical Wnt signalling to be inhibited from the very start of in vitro otic differentiation in order for it to have its upregulatory effect. FIG. 4 shows the effect of supplementing the FGF medium with canonical Wnt inhibitors from day 4 of the otic differentiation protocol on gene expression of PAX2, PAX8 and FOXG1, and FIG. 5 displays the outcome on the ectoderm (A), mesoderm (B) and endoderm (C) germ layer marker gene expression. It was observed that inhibiting canonical Wnt signalling with any of the three small molecule compounds from day 4 of the standard 12 day otic differentiation protocol did not lead to an upregulation of the otic markers or ectodermal lineage markers compared to the FGF condition, as seen when canonical Wnt was inhibited from the start of the differentiation protocol. Conversely gene expression of mesoderm and endoderm markers, previously seen to be significantly downregulated upon canonical Wnt inhibition from the start of differentiation, was significantly upregulated with the supplementation of at least one of the small molecule compounds from day 4 of differentiation. This is suggesting the initiation of canonical Wnt signalling inhibition must take place from the start of hES cell differentiation in order for it to have a positive effect on upregulating gene expression of otic specific markers.

1.4 Canonical Wnt Signalling Inhibition in Combination with FGF 3 and FGF 10 is not Required for the Duration of Otic Differentiation In Vitro Thus far the inventors have demonstrated that inhibition of canonical Wnt signalling must occur from the very start of the protocol in order to promote gene expression of ectodermal lineage markers and upregulation of the key otic markers, PAX2, PAX8 and FOXG1. Concomitantly a downregulation of mesoderm and endoderm marker gene expression is also observed when canonical Wnt signalling is present for the full 12 days of the protocol. These effects are essentially reversed when inhibition takes place from day 4.

Figure 6:
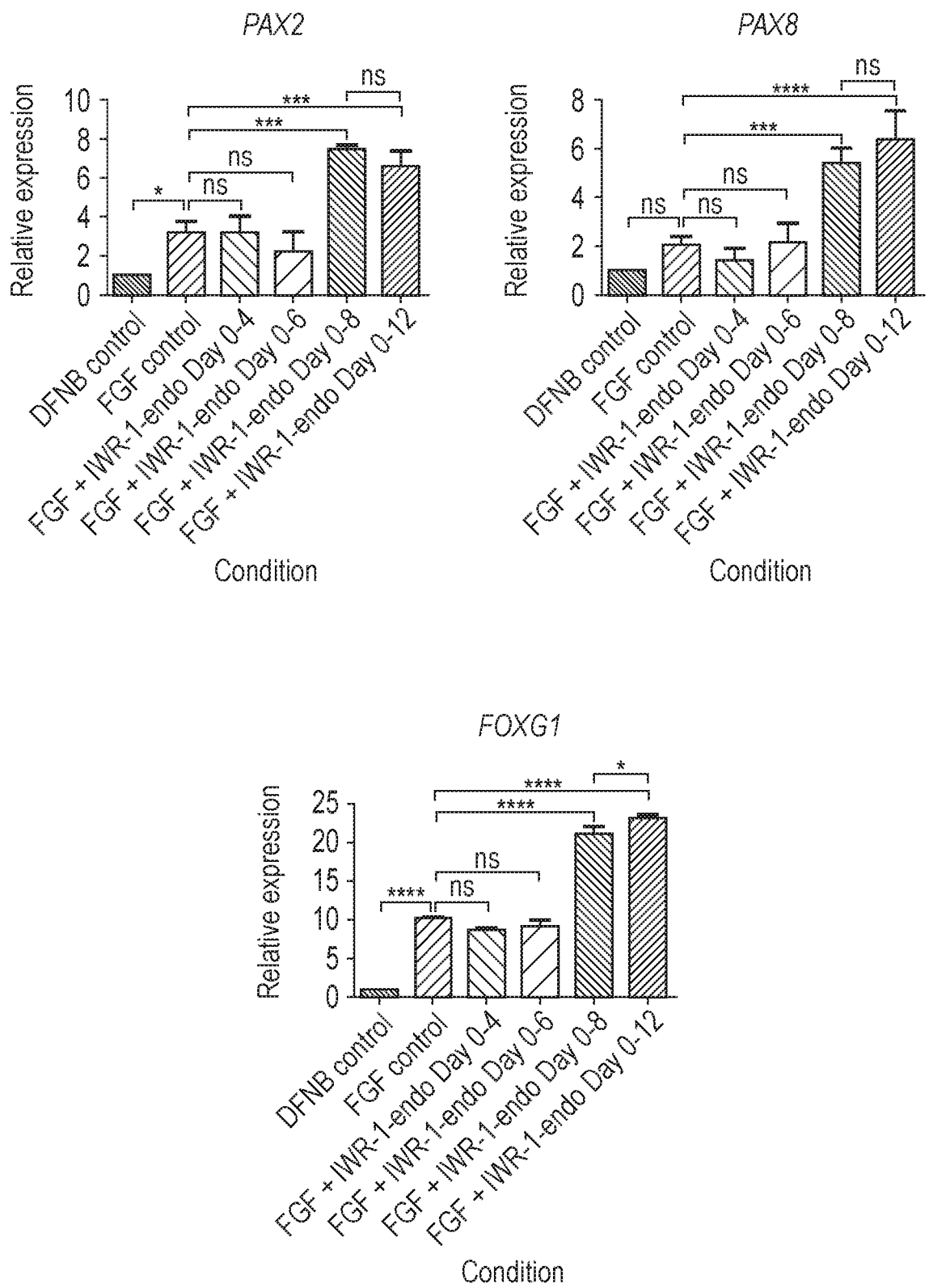
FIG. 6 shows gene expression of otic markers PAX2, PAX8 and FOXG1 following a 12 day differentiation protocol with H14S9 hES cells, seeded at $8 \times 10^3$ cells/cm$^2$. IWR-1-endo was supplemented at day 0 and maintained to day 4, day 6, day 8 or day 12. Gene expression is presented as relative to that of the DFNB baseline control. Bar charts denote mean and standard deviation of gene expression relative to that of the DFNB control condition (n=3 independent experiments). Statistical significance was determined by one way ANOVA with Bonferroni's multiple comparison post-test. ns=no significant difference. *P<0.05, *P<0.001, **P<0.0001.

Further investigating the timing of canonical Wnt inhibition it was important to address whether inhibition was required throughout the whole 12-day differentiation protocol. Experiments were set up to inhibit canonical Wnt signalling for different lengths of time. In combination with FGF medium, Wnt inhibition took place from day 0 to day 4, day 0 to day 6, or day 0 to day 8. Differentiating cells were maintained in FGF medium-only following day 4, 6 or 8, respectively until day 12. Day 0 to day 12 inhibition was also included as shown in previous figures. At the end of day 12, gene expression of PAX2, PAX8 and FOXG1 was quantified relative to the DFNB baseline condition, and is shown in FIG. 6. As the effects on gene expression of IWR-1-endo was similar in all experiments carried out previously, and with IWR-1-endo being well established in the literature, all future experiments were carried using IWR-1-endo as the canonical Wnt inhibitor of choice. Inhibiting canonical Wnt signalling with IWR-1-endo from day 0 to day 4 or day 0 to day 6 did not significantly alter gene expression of PAX2, PAX8 or FOXG1 from that of FGF medium alone. Significant upregulation of the otic markers was only found between the standard FGF medium and FGF with canonical Wnt inhibition from day 0 to 8 or day 0 to 12. Moreover, there was no significant difference on otic marker gene expression between inhibiting Wnt signalling from day 0 to day 8 or throughout the whole 12 day differentiation protocol (for PAX2 and PAX8-FOXG1 gene expression was significantly higher with 12 days of canonical Wnt inhibition in contrast to eight days however). Therefore canonical Wnt inhibition is required from the initiation of hES differentiation, and must be maintained for longer than 6 days (preferably at least eight days) to elicit an upregulatory response of the key otic marker gene expression.

2. Wnt Manipulation During Late Otic Differentiation 2.1 Canonical Wnt Signalling Activation Late in Otic Differentiation in the Presence of FGF Signalling Leads to Loss of Otic Marker Gene Expression Results described above demonstrated that inhibition of canonical Wnt signalling enhances the induction of ectodermal fate and subsequent expression of otic genes when inhibition is carried out from the start of the otic differentiation protocol. In addition, canonical Wnt signalling needs to be inhibited for longer than 6 days (preferably at least eight days) to have this upregulatory effect on the ectodermal and otic marker gene expression. Inhibition of canonical Wnt signalling from day four of the protocol showed a downregulation or loss of ectodermal and otic gene expression, with differentiation favouring a more mesodermal and endodermal fate.

Taking these data into account it was hypothesised that the increase in ectodermal differentiation with canonical Wnt inhibition was permissive for the supplemented FGF 3 and FGF 10 ligands to induce the otic fate. The role of Wnt signalling in otic placode development is less well characterised than the role of FGF signalling (Freyer and Morrow, 2010, Jacques et al., 2012, Vendrell et al., 2013), but activation of the canonical pathway is believed to be involved in the expansion of the otic placode size once it has been induced (Ohyama et al., 2006). Therefore it was of most interest to determine if the otic marker gene expression could be enhanced further by incorporating a period of canonical Wnt activation into the differentiation protocol.

Otic differentiation experiments were set up comprising of a phase of canonical Wnt inhibition for eight days with 10 µM IWR-1-endo, then a switch to activation with 2 µM BIO for the remaining four days of the protocol. FGF 3 and FGF 10 were supplemented throughout the full 12 days of differentiation. From here on this modified protocol will be referred to as Modified Protocol 1. Standard DFNB (Control) and FGF conditions were also included. At the end of the differentiation period gene expression analysis was carried out by QPCR. The DFNB baseline condition was used as the reference calibrator. For ease of understanding, FIG. 7 shows a schematic representation of Modified Protocol 1 (A) and the relative gene expression of the otic markers PAX2, PAX8, FOXG1 and SOX2 (B).

Unexpectedly, the combination of FGF ligands and canonical Wnt activation during the last four days of the manipulated otic differentiation protocol (Modified Protocol 1) caused a highly statistically significant downregulation of all otic markers investigated, compared to the previous eight day Wnt inhibition protocol (FIG. 6). In addition, in the case of PAX2 and FOXG1 there was no significant difference in the gene expression between the standard FGF protocol used herein and Modified Protocol 1. In light of the published data on the role of canonical Wnt signalling in otic placode expansion in vivo, these results were surprising. However the work of Freter et al. (Freter et al., 2008) has proposed an inhibitory role of continuous FGF signalling during otic placode maturation and expansion when canonical Wnt signalling is active. In this study in the chick it was demonstrated that an attenuation of Fgf 3 and Fgf 19 signalling is required for otic commitment.

Figure 8A:
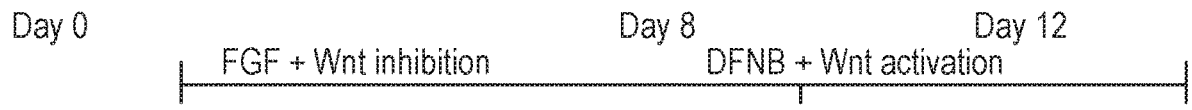
FIG. 8 provides a schematic representation of Modified Protocol 2 (A). Gene expression of otic markers PAX2, PAX8, FOXG1 and SOX2 following a 12 day differentiation protocol with H14S9 hES cells, seeded at $8 \times 10^3$ cells/cm$^2$ (B). Canonical Wnt inhibition is via 10 µM IWR-1-endo and activation via 2 µM BIO. FGF 3 and FGF 10 ligands are supplemented at 50 ng/ml. Gene expression is presented as relative to that of the DFNB baseline control. Bar charts denote mean and standard deviation of gene expression relative to that of the DFNB control condition (n=3 independent experiments). Statistical significance was determined by one way ANOVA with Bonferroni's multiple comparison post-test. ns=no significant difference. *P<0.05, P<0.01, *P<0.001, ****P<0.0001.

2.2 Canonical Wnt Activation with Removal of Supplemented FGF Ligands in Late Otic Differentiation Leads to Upregulation of PAX2, PAX8 and FOXG1, with a Loss of SOX2 Expression In light of the data shown by Freter et al. (Freter et al., 2008) another alteration to the Wnt manipulation protocol was tested. This protocol involved the initial eight day period of FGF 3 and FGF 10 ligand supplementation with canonical Wnt signalling inhibition with IWR-1-endo. For the remaining four days canonical Wnt activation was carried out with BIO in the DFNB basal medium. FGF 3 and FGF 10 were not supplemented into the medium during these last four days of the protocol (featured in Modified Protocol 1). This alternate protocol will be referred to from here on as Modified Protocol 2, and is schematically represented in FIG. 8A.

The effect of Modified Protocol 2 (FIG. 8B) on the gene expression of PAX2, PAX8 and FOXG1 was positive, leading to a significant upregulation of these otic markers when compared to the FGF and initial eight day Wnt inhibition protocol. Therefore in this case the removal of FGF 3- and FGF 10-ligand supplementation during the canonical Wnt activation phase was beneficial for the differentiation and gene expression of these markers. However a striking feature of this modified protocol was the highly significant downregulation of the gene expression of SOX2. In the Modified Protocol 1 experiment (FIG. 7B) with canonical Wnt activation and FGF 3 and FGF 10 ligand supplementation, SOX2 gene expression was downregulated alongside the other otic markers investigated. SOX2 gene expression is also downregulated during the final four days of Modified Protocol 2 (FIG. 8B), when canonical Wnt activation takes place with no concomitant FGF ligand supplementation. These experiments, performed side by side, suggested that FGF signalling during the final four days of the modified protocols is required at a particular level in order for otic differentiation to progress. Maintaining FGF 3 and FGF 10 at the standard 50 ng/ml concentration throughout the phase of canonical Wnt activation with BIO appears to be inhibitory to the gene expression of PAX2, PAX8, FOXG1 and SOX2 (FIG. 7B). However, withdrawing FGF 3 and FGF 10 from the differentiation media during canonical Wnt activation (FIG. 8B) upregulates PAX2, PAX8 and FOXG1 gene expression, but is still detrimental for expression of SOX2. It could consequently be hypothesised that a "Goldilocks" effect of FGF signalling is taking place in otic differentiation in the presence of Wnt activation; too much FGF appears to be inhibitory for PAX2, PAX8 and FOXG1 expression, while some FGF maybe be needed for SOX2 expression, a key regulator of downstream development of the inner ear structures.

Figure 9A:
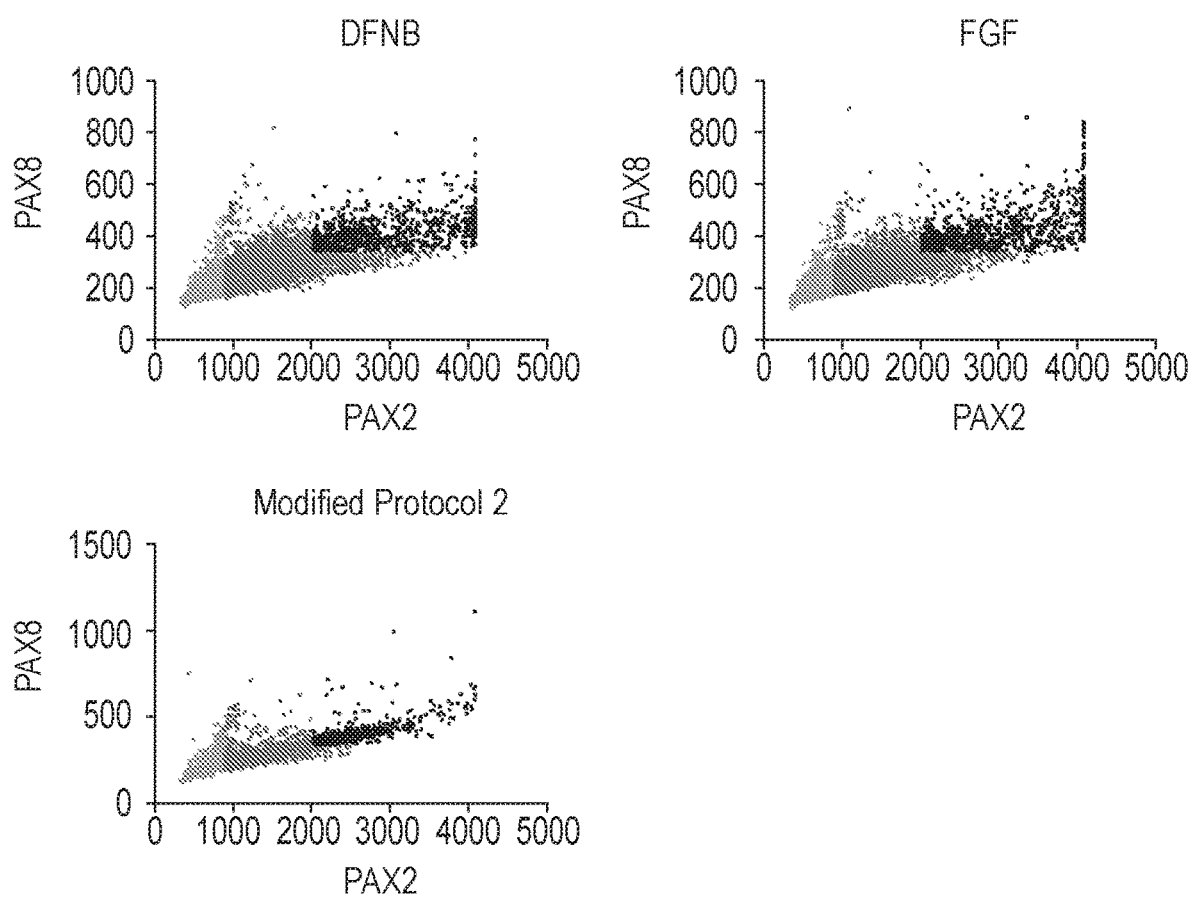
FIG. 9 provides data for H14S9 hES cells differentiated for 12 days in DFNB, FGF or subjected to the Modified Protocol 2. Representative experiment displayed below. Scatterplots for immunolabelling with (A) PAX2/PAX8 (green/red), (B) FOXG1/PAX8 (green/red) and (C) SOX2/PAX8 (green/red). Fluorescence intensity of each antibody is displayed on each axis. The scatter plots are coloured according to two different intensity thresholds: 99th percentile points of fluorescent intensity in the secondary antibody only control, and 75$^{th}$ percentile points of fluorescent intensity seen in the FGF condition labelling. Grey: intensity below 99$^{th}$ percentile. Green: intensity above the 99$^{th}$ percentile for the green (PAX2, FOXG1, SOX2) but not red channel (PAX8). Red: intensity above the 99$^{th}$ percentile in the red channel but not green channel. Purple: cells are double positive, intensity above the 99$^{th}$ percentile in both channels. Black: cells are highly double positive, intensity is above the FGF 75$^{th}$ percentile in both channels.
Figure 9B:
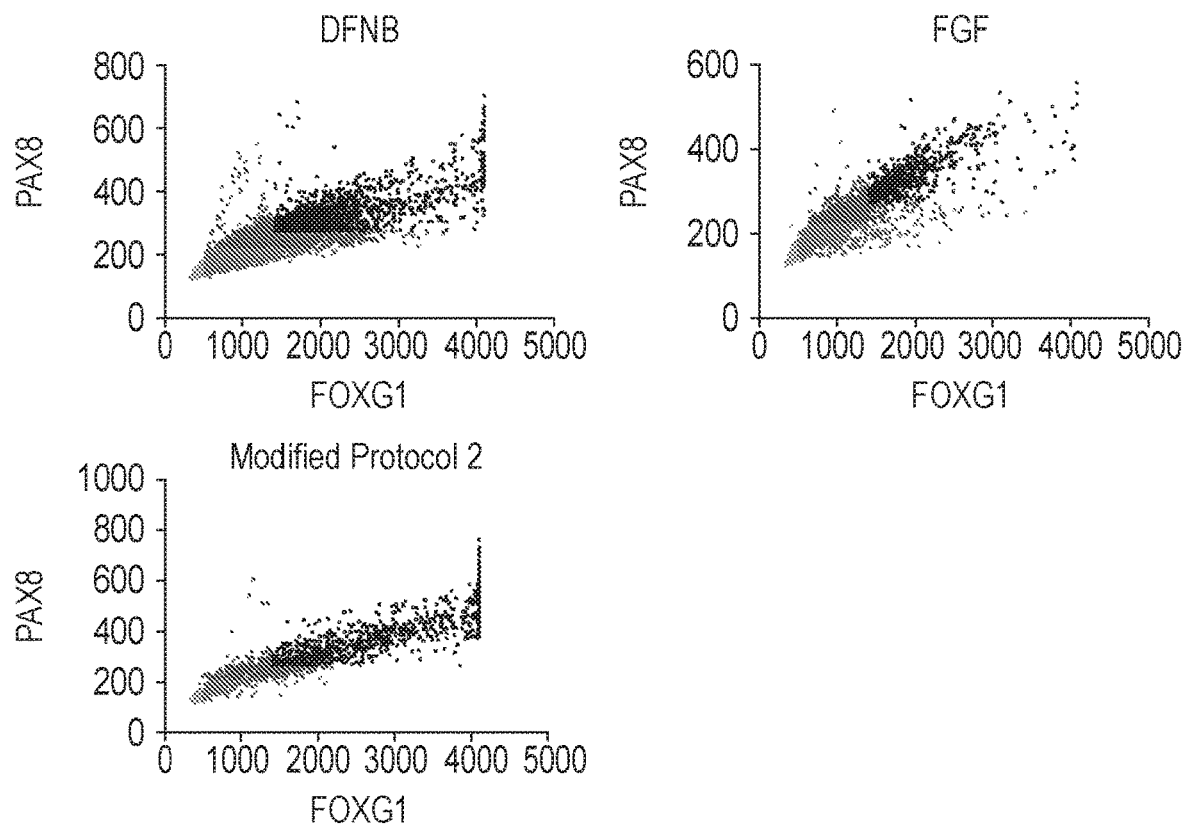
Figure 9C:
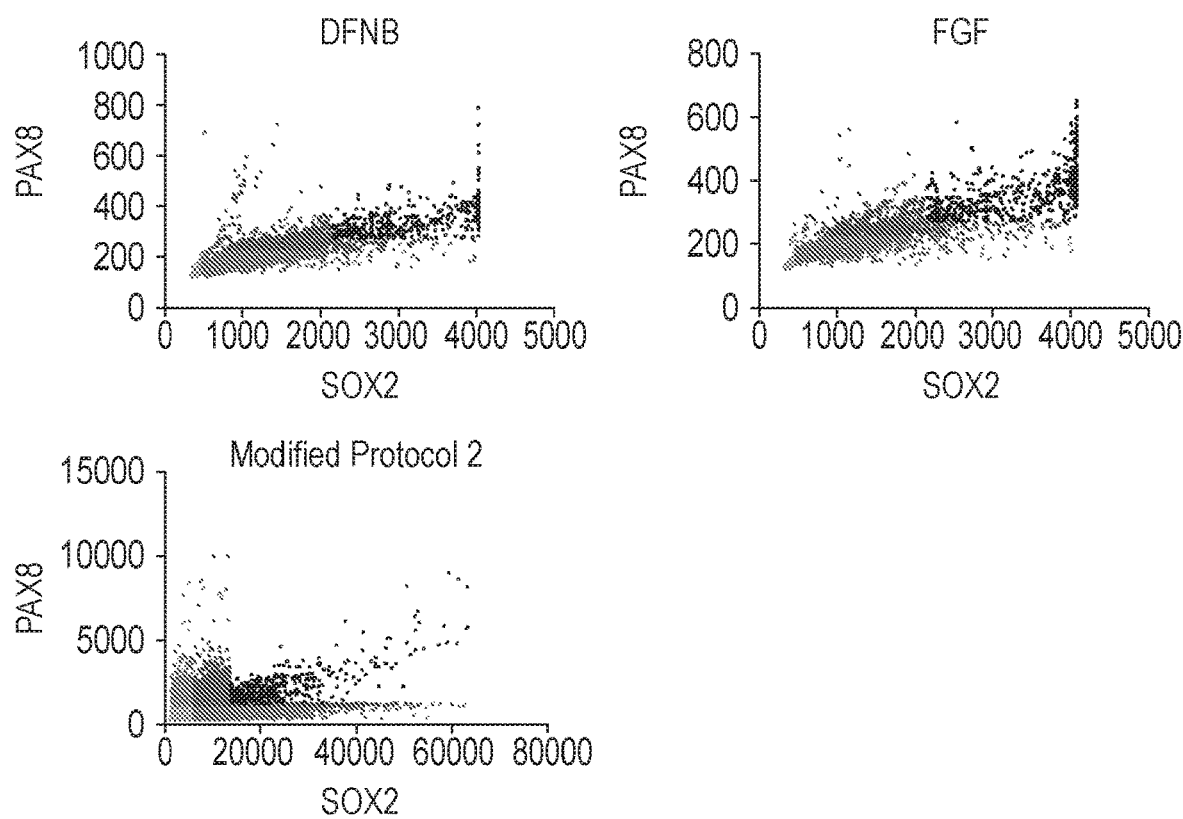
Figure 10:
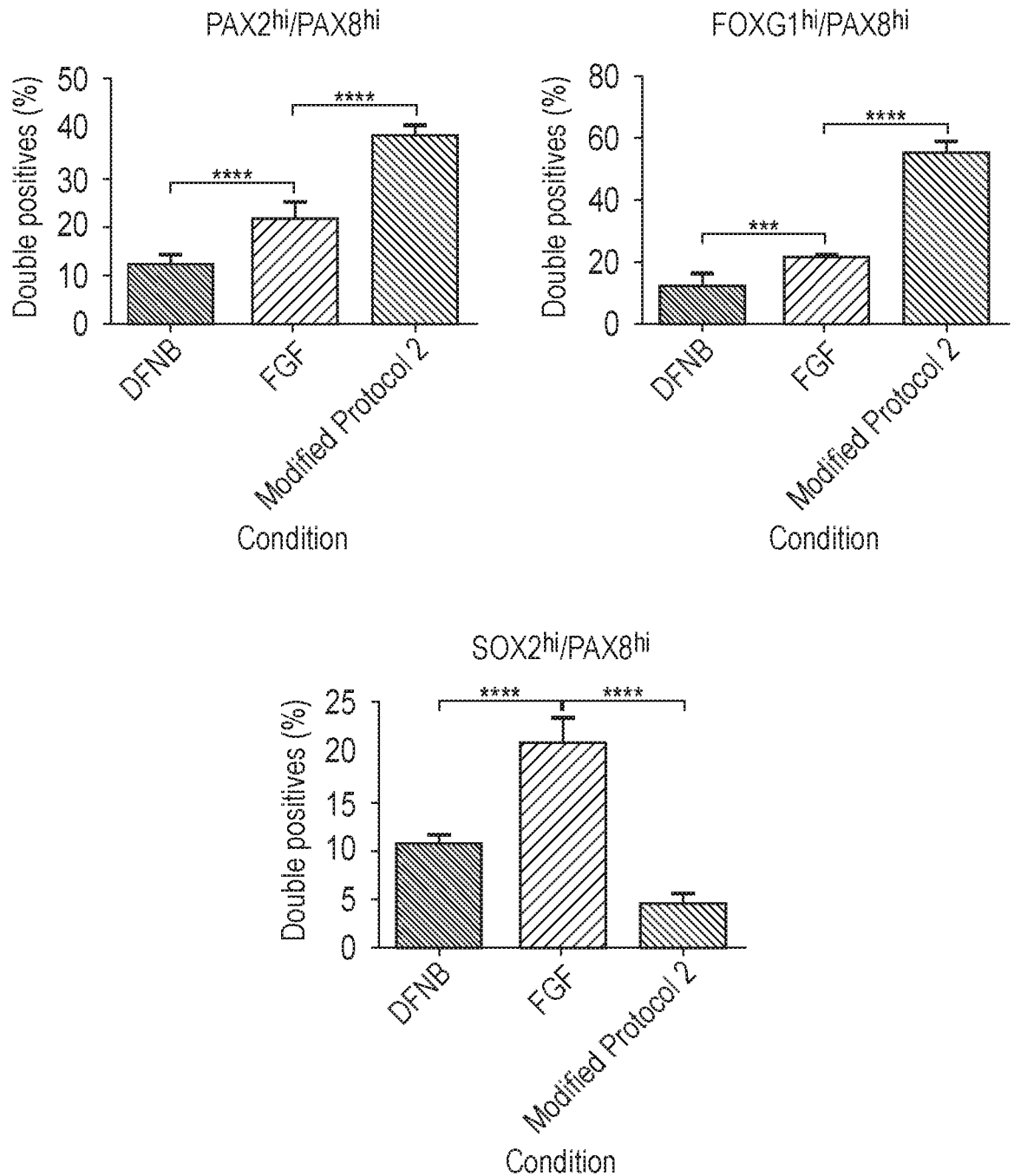
FIG. 10 provides data for H14S9 hES cells differentiated for 12 days in DFNB, FGF or subjected to Modified Protocol 2. Bar charts show the percentage of highly double positive cells (with a threshold intensity above the 75th percentile) in each condition for the antibody combinations PAX2$^{hi}$/PAX8$^{hi}$, FOXG1$^{hi}$/PAX8$^{hi}$, and SOX2$^{hi}$/PAX8$^{hi}$. The results are presented as the mean of three experimental replicates combined. Error bars denote mean and standard deviation. Statistical significance was determined using Chi-square with Yates' continuity correction. *P<0.001, **P<0.0001.

As Modified Protocol 2 appears to be the most efficient protocol in the upregulation of the majority of the otic marker gene expression, this protocol was looked at in greater detail. To determine if the loss of SOX2 gene expression (and also the upregulation of the other otic markers) is just at the level of RNA, it is important to also investigate protein expression. Analysis of the protein expression was done using the In Cell Analyser 1000 platform. Differentiation experiments were carried out with H14S9 hES cells subjected to DFNB, FGF and the Modified Protocol 2 conditions. Following the 12 day differentiation period cells were immunolabelled with the following combinations of primary antibodies (a representative experiment is displayed in FIG. 9): PAX2/PAX8 (A), FOXG1/PAX8 (B) and SOX2/PAX8 (C). Results of three independent repeat experiments are shown in FIG. 10. The In Cell Analyser platform was used to determine the percentage of highly co-expressing cells believed to represent the true otic progenitor population with the differentiating cultures. Cells were deemed to be highly co-expressive of the otic marker antibody combinations if their fluorescent intensity threshold was above the $75^{th}$ percentile set within the FGF condition.

The results of the three independent experiments presented in FIG. 10 show, as expected, a statistically significant upregulation of otic marker protein expression between the baseline DFNB control and the FGF treated conditions. The percentage of highly double positive cells for the DFNB, FGF and Modified Protocol 2 conditions respectively for each pair of antibodies used were as follows: PAX2/PAX8: 12.08%±2.02%, 21.20%±3.78%, and 38.17%±2.21%; FOXG1/PAX8: 12.21%±4.27%, 21.31%±0.97%, and 54.75%±4.03%; SOX2/PAX8: 10.41%±1.1%, 20.76%±2.53%, and 4.30%±1.25%. By looking at these results it is apparent that the difference in gene expression levels between the DFNB, FGF and Modified Protocol 2 conditions as shown by QPCR (FIG. 8) is also demonstrated in the percentage of highly double positive cells for each otic marker antibody combination. Compared to the standard FGF differentiation protocol used herein, Modified Protocol 2 appears to generate a significantly higher proportion of differentiated otic progenitors which highly express the characteristic otic markers PAX2, PAX8 and FOXG1, both at the RNA and protein levels. SOX2 RNA and protein expression, however, are significantly downregulated with Modified Protocol 2.

Figure 11:
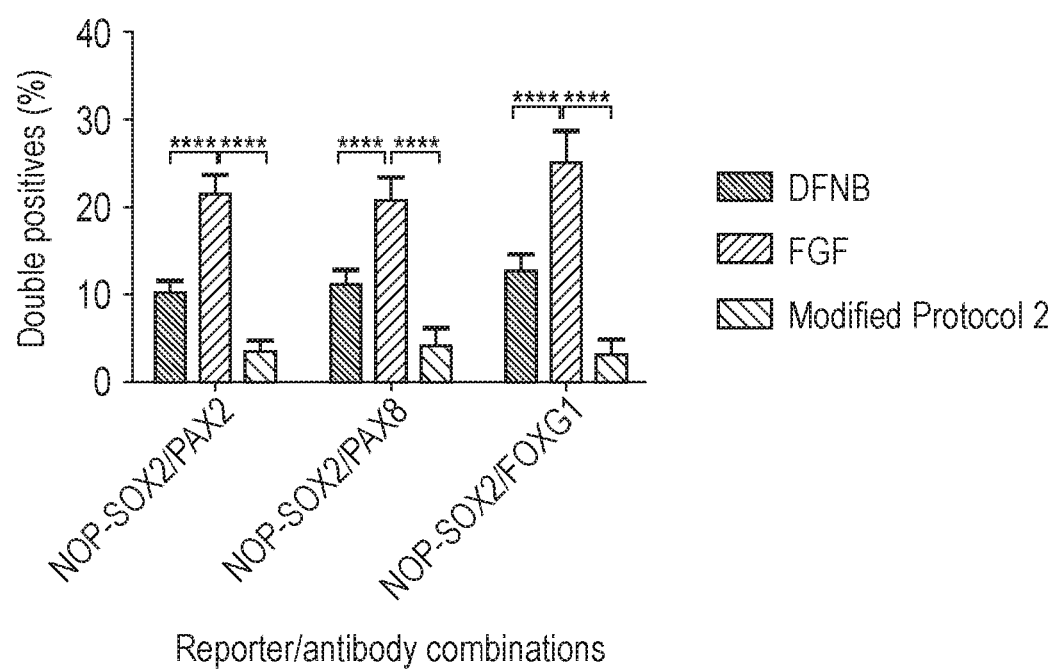
FIG. 11 shows co-staining of H14S9 NOP-SOX2 reporter cells differentiated for 12 days in DFNB, FGF or Modified Protocol 2 conditions. Cells were immunolabelled with PAX2, PAX8 or FOXG1 primary antibodies, and the percentage of double positive cells (primary antibody and NOP-SOX2 GFP) is shown below (n=3 independent experiments). Error bars denote mean and standard deviation. Statistical significance was determined using Chi-square with Yates' continuity correction. ****P<0.0001.

Subsequently, for further confirmation of the effect of Modified Protocol 2 on the expression of SOX2, differentiation experiments were set up using an hESC line that reports on otic expression of SOX-2, the H14S9 NOP-50×2 reporter line. Reporter line cells were differentiated for 12 days in DFNB, FGF or Modified Protocol 2 conditions, followed by immunolabelling with PAX2, PAX8 or FOXG1 antibodies. The percentage of differentiated cells co-expressing the otic markers with NOP-SOX2 enhancer driven GFP from all three conditions tested are displayed in FIG. 11. Following the 12 day differentiation period, the percentage of cells co-expressing an otic marker alongside NOP-SOX2 enhancer driven GFP from each of the tested conditions (DFNB, FGF and Modified Protocol 2 respectively) was observed as follows: NOP-SOX2/PAX2: 10.55%±1.22%, 21.88%±2.02% and 3.83%±1.14%; NOP-SOX2/PAX8: 11.58%±1.56%, 21.25%±2.51%, and 4.62%±1.78%; NOP-SOX2/FOXG1: 13.18%±1.70%, 25.46%±3.53%, and 3.52%±1.51%. As with the antibody immunolabelling in FIGS. 9A and 10, co-expression of any of the otic markers with the NOP-SOX2 GFP was significantly lower when the reporter hES cells were differentiated in Modified Protocol 2, compared to the DFNB baseline and the standard FGF condition. It can be concluded that the low percentages seen in FIG. 11 are as a result of the decreased NOP-SOX2 enhancer reporter activity, and thus SOX2 expression. Expression of PAX2, PAX8 and FOXG1, as seen in FIGS. 9A and 10, increased during differentiation in Modified Protocol 2 condition and so this also adds weight to the suggestion that it is indeed solely SOX2 expression that is being affected detrimentally in Modified Protocol 2.

Figure 7A:
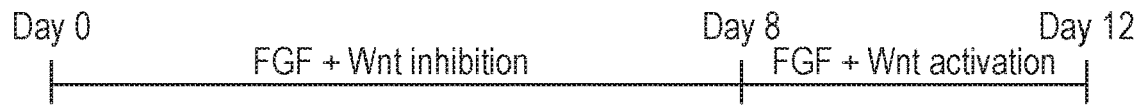
FIG. 7 provides a schematic representation of Modified Protocol 1 (A). Gene expression of otic markers PAX2, PAX8, FOXG1 and SOX2 following a 12 day differentiation protocol with H14S9 hES cells, seeded at $8 \times 10^3$ cells/cm$^2$ (B). Canonical Wnt inhibition is via 10 µM IWR-1-endo and activation via 2 µM BIO. FGF 3 and FGF 10 ligands are supplemented at 50 ng/ml. Gene expression is presented as relative to that of the DFNB baseline control. Bar charts denote mean and standard deviation of gene expression relative to that of the DFNB control condition (n=3 independent experiments). Statistical significance was determined by one way ANOVA with Bonferroni's multiple comparison post-test. ns=no significant difference. *P<0.05, P<0.01, *P<0.001, ****P<0.0001.
Figure 7B:
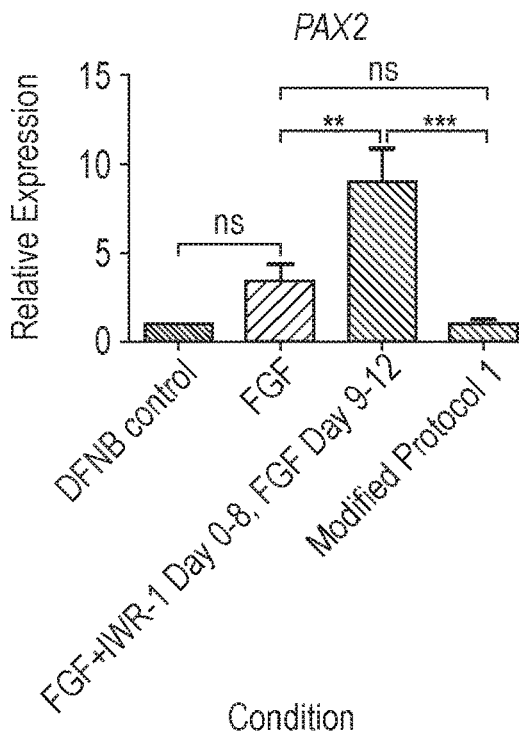
Figure 7B:
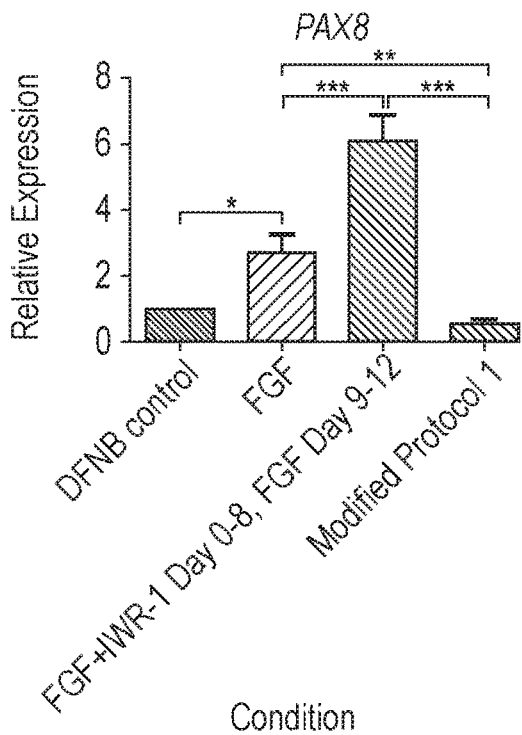
Figure 7B:
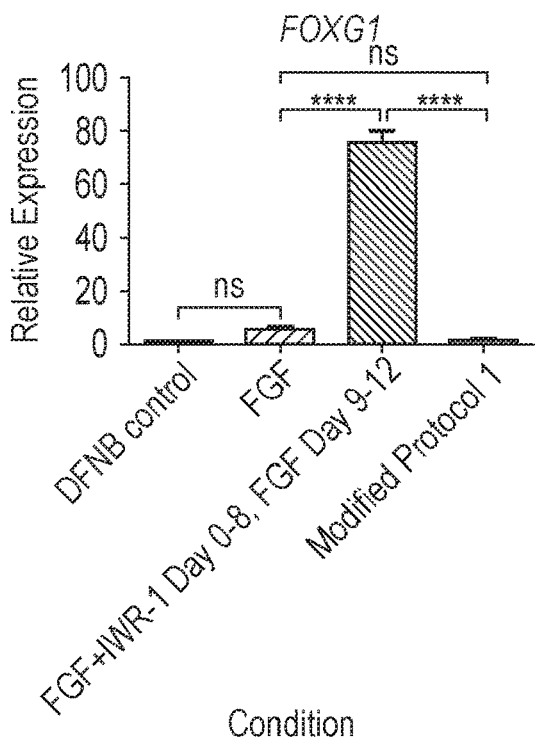
Figure 7B:
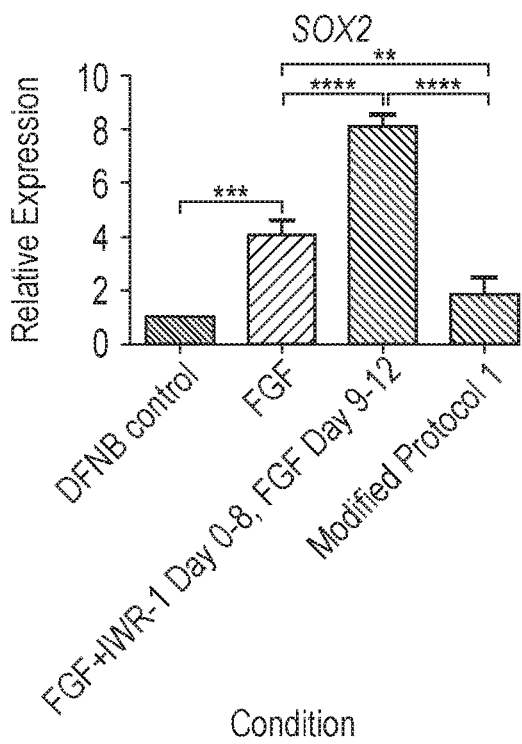
Figure 8B:
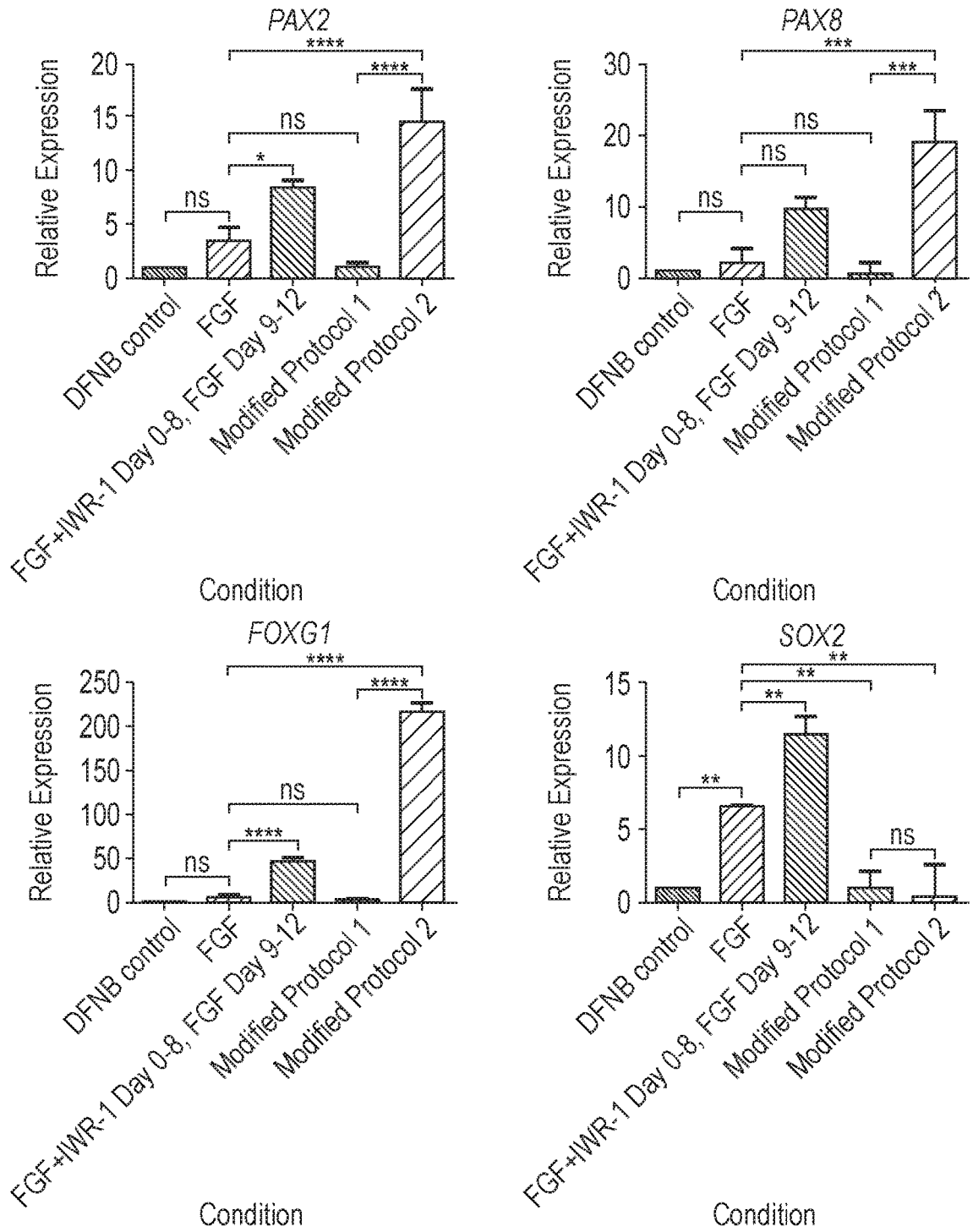

2.3 FGF Ligand Supplementation at a Lowered Dose During Canonical Wnt Activation in Late Otic Differentiation Maintains the Upregulation of PAX2, PAX8 and FOXG1, and Rescues SOX2 Expression It has been shown previously in this section that in a 12 day differentiation protocol maintaining FGF 3 and FGF 10 ligand supplementation throughout the period of Wnt inhibition (eight days) and subsequent Wnt activation (four days) (Modified Protocol 1) leads to a loss or downregulation of gene expression of PAX2, PAX8, FOXG1 and SOX2 (FIGS. 7A and 7B). An alternative version of the protocol was tested in which FGF 3 and FGF 10 ligands were not supplemented into the media during the four day period of canonical Wnt activation (Modified Protocol 2). From this alternate protocol it was observed that gene expression of PAX2, PAX8 and FOXG1 was significantly upregulated compared to the standard FGF or any other modifications of the protocol tested, yet SOX2 gene expression was significantly downregulated (FIGS. 8A and 8B). Matching the RNA expression, a similar outcome of Modified Protocol 2 was also observed in otic marker protein expression (FIGS. 9A and 10), and also upon differentiating the H14S9 NOP-SOX2 reporter cells (FIG. 11). In summary, maintenance of FGF supplementation during the canonical Wnt activation phase of the protocol has a negative impact on otic differentiation, whereas removal of FGF ligands is beneficial for all otic marker expression except for SOX2, suggesting an intermediate level of FGF signalling may be required.

Figure 12A:
FIG. 12 provides a schematic representation of Modified Protocol 3 (A). Gene expression of otic markers PAX2, PAX8, FOXG1 and SOX2 following a 12 day differentiation protocol with H14S9 hES cells, seeded at $8 \times 10^3$ cells/cm$^2$ (B). Canonical Wnt inhibition is via 10 µM IWR-1-endo and activation via 2 µM BIO. FGF 3 and FGF 10 ligands are supplemented at 50 ng/ml or 25 ng/ml where appropriate. Gene expression is presented as relative to that of the DFNB baseline control. Bar charts denote mean and standard deviation of gene expression relative to that of the DFNB control condition (n=3 independent experiments). Statistical significance was determined by one way ANOVA with Bonferroni's multiple comparison post-test. ns=no significant difference. *P<0.05, P<0.01, *P<0.001, ****P<0.0001.
Figure 12B:
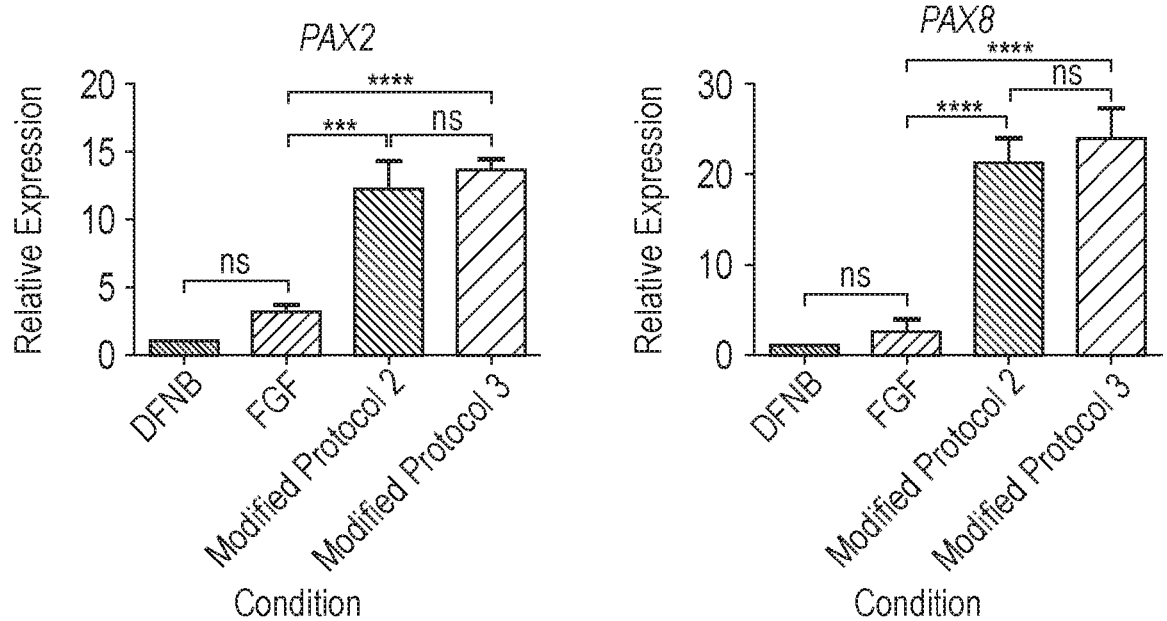

To address the possibility of an intermediate level of FGF signalling requirement to enhance otic differentiation, differentiation experiments were set up as follows. As with the previous incarnations of the protocol, FGF 3 and FGF 10 were supplemented into the basal DFNB medium at a concentration of 50 ng/ml with concomitant canonical Wnt inhibition with IWR-1-endo at 10 µM, with the hES cells differentiating in this condition for eight days. For the final four days of the protocol, cells were maintained in DFNB medium supplemented with the canonical Wnt agonist BIO at a concentration of 2 µM, and FGF 3 and FGF 10 supplemented at 25 ng/ml (half of the concentration used in the standard otic differentiation protocol and previous modifications). This version of the protocol will be referred to as Modified Protocol 3 from here on. A schematic of the protocol is displayed in FIG. 12A. Differentiation experiments with Modified Protocol 3 were carried out alongside H14S9 hES cells differentiated in DFNB, FGF or Modified Protocol 2 conditions. QPCR analysis of otic marker gene expression was carried out and the results are displayed in FIG. 12B. It was observed that Modified Protocol 3 reproducibly leads to the differentiation of otic progenitors with a significant upregulation of the gene expression of the otic markers PAX2, PAX8, FOXG1 and SOX2. For PAX2, PAX8 and FOXG1 the difference in gene expression between Modified Protocol 2 and 3 is not statistically significant, suggesting that the expression of these genes has become independent of FGF by this stage, and can be sustained with Wnt activation. Moreover, the gene expression of SOX2 in the Modified Protocol 3 is rescued and significantly increased over the expression observed from Modified Protocol 2. For SOX2, this result suggests an intermediate level of FGF signalling must take place during canonical Wnt activation in order to upregulate and maintain its expression.

Figure 12B:
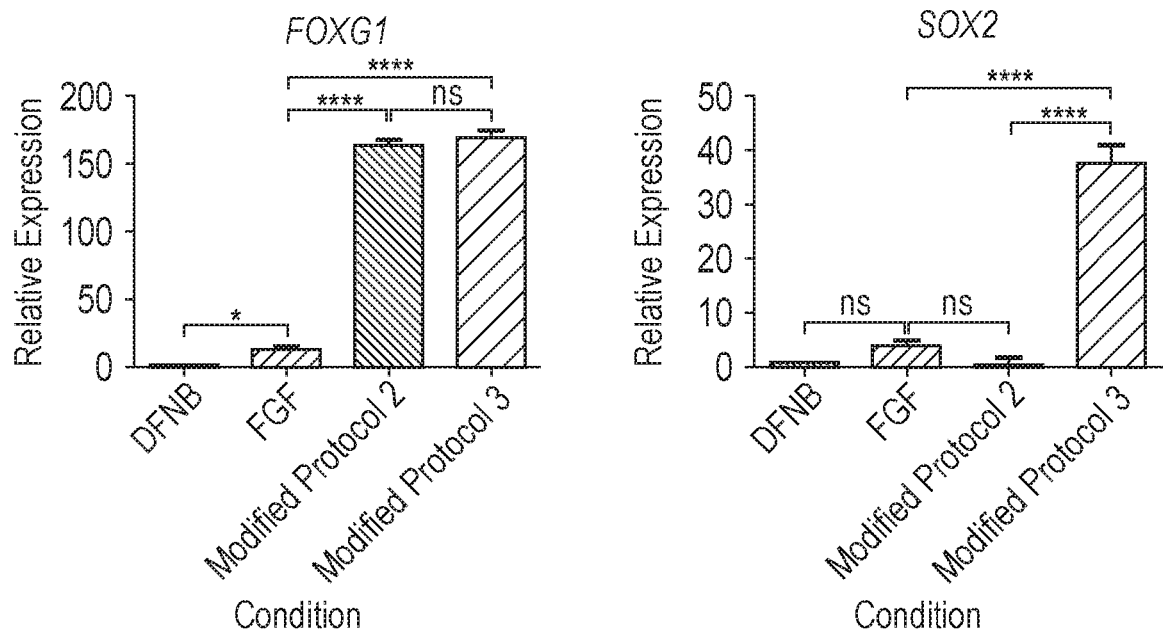
Figure 13:
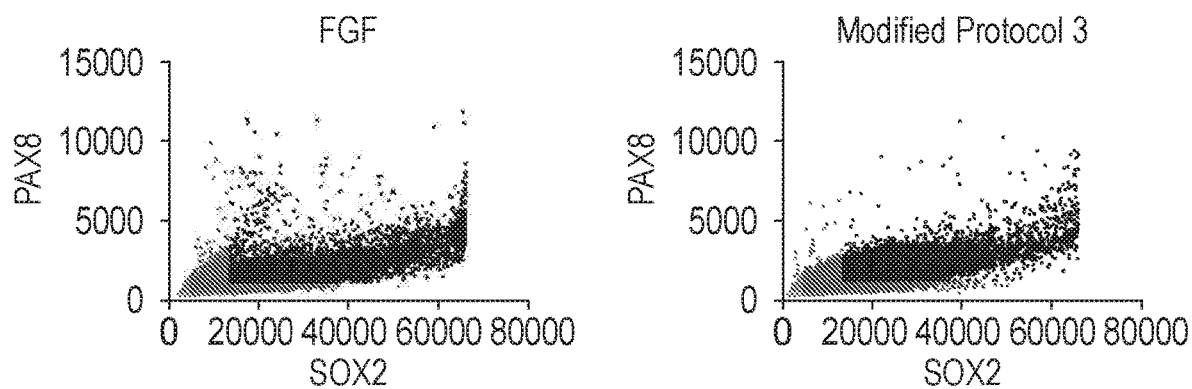
FIG. 13 shows data for H14S9 hES cells differentiated for 12 days in FGF or subjected to the Modified Protocol 3. Representative experiment displayed below. Scatterplots for immunolabelling with SOX2/PAX8 (green/red). Fluorescence intensity of each antibody is displayed on each axis. The scatter plots are coloured according to two different intensity thresholds: 99th percentile points of fluorescent intensity in the secondary antibody only control, and 75$^{th}$ percentile points of fluorescent intensity seen in the FGF condition labelling. Grey: intensity below 99$^{th}$ percentile. Green: intensity above the 99$^{th}$ percentile for the green (SOX2) but not red channel (PAX8). Red: intensity above the 99$^{th}$ percentile in the red channel but not green channel. Purple: cells are double positive, intensity above the 99th percentile in both channels. Black: cells are highly double positive, intensity is above the FGF 75th percentile in both channels.
Figure 14:
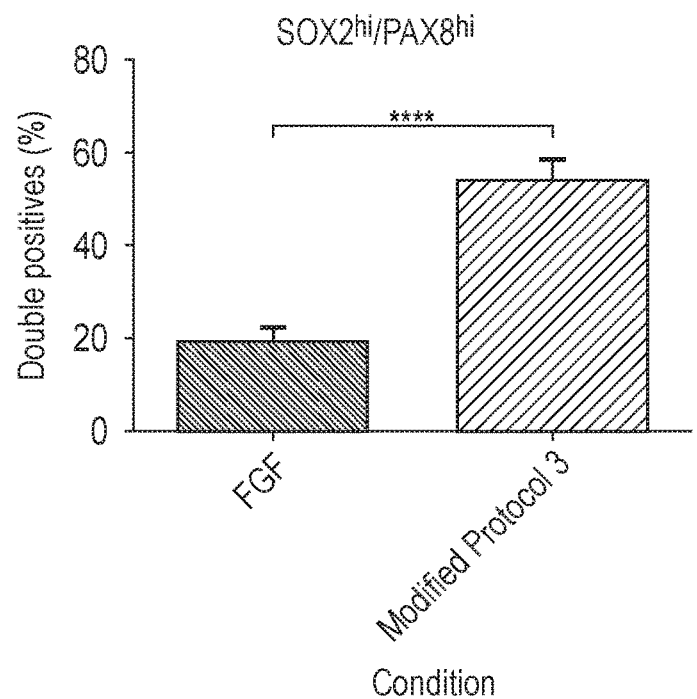
FIG. 14 shows data for H14S9 hES cells differentiated for 12 days in FGF or subjected to Modified Protocol 3. Bar charts show the percentage of highly double positive cells (with a threshold intensity above the 75th percentile) in each condition for the antibody combination SOX2$^{hi}$/PAX8$^{hi}$. The results are presented as the mean of three experimental replicates combined. Error bars denote mean and standard deviation. Statistical significance was determined using Chi-square with Yates' continuity correction. ****P<0.0001.

The In Cell Analyser 1000 platform was next used to ascertain whether the rescue of SOX2 gene expression at the RNA level was mirrored in the protein level via antibody immunolabelling. The standard FGF condition was used as a baseline in these experiments and PAX8 was used as the co-expressing marker. FIG. 13 displays a representative example of the In Cell Analyser results, with three independent experimental repeats shown in FIG. 14. Across the repeat experiments the differentiating cells in the FGF condition were observed to have a typical percentage of highly double positive cells for the otic marker combination of SOX2 and PAX8 as seen in previous experiments (mean of 19.6%±2.90%). The percentage of cells highly double positive for this combination of markers from the Modified Protocol 3 condition, however, was found to be a mean of 53.98%±4.47%. This is a considerable rescue and increase of SOX2 protein expression when compared with Modified Protocol 2 (FIG. 10), and is consistent with the upregulation of SOX2 gene expression seen in FIG. 12 by QPCR analysis.

Figure 15:
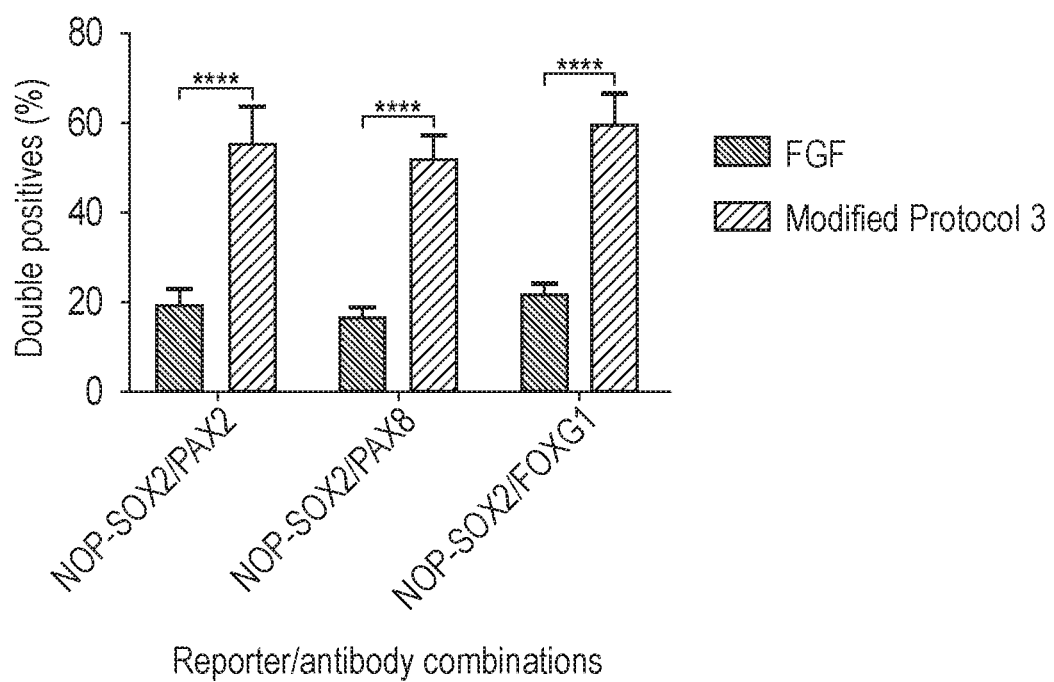
FIG. 15 shows co-staining of H14S9 NOP-SOX2 reporter cells differentiated for 12 days in FGF or Modified Protocol 3 conditions. Cells were immunolabelled with PAX2, PAX8 or FOXG1 primary antibodies, and the percentage of double positive cells (primary antibody and NOP-SOX2 GFP) is shown below (n=3 independent experiments). Error bars denote mean and standard deviation. Statistical significance was determined using Chi-square with Yates' continuity correction. ****P<0.0001.

Additionally H14S9 NOP-SOX2 reporter hES cells were also differentiated in both the FGF and Modified Protocol 3 conditions and PAX2, PAX8 and FOXG1 otic marker expression co-labelling with the NOP-SOX2 enhancer driven GFP was investigated. Three experiments were carried out and are displayed in FIG. 15. In agreement with the antibody immunolabelling in FIG. 12, NOP-SOX2 enhancer driven GFP co-labelling with PAX2, PAX8 and FOXG1 was significantly increased when the cells were differentiated in Modified Protocol 3 compared to the standard FGF protocol (FIG. 15), and is in contrast to the outcome of Modified Protocol 2 on NOP-SOX2 enhancer activity (FIG. 11). The mean percentage of NOP-SOX2 GFP positive cells with highly positive otic marker antibody immunolabelling for FGF and Modified Protocol 3 respectively were observed as follows: NOP-SOX2/PAX2: 19.59%±3.31% and 55.79%±7.90%; NOP-SOX2/PAX8: 16.94%±1.82% and 52.31%±5.07%; NOP-SOX2/FOXG1: 22.04%±2.14% and 59.83%±6.73%.

Example of Detailed Protocol for the Generation of Otic Progenitors from hESCs (Modified Protocol 3)

Phase 1 (12 days)

Previous day: coat dishes with laminin 2 µg/cm$^2$: 22 µl laminin/2 ml ice cold PBS/35 mm dish (8.8 cm$^2$); T12.5 flasks with 2.5 µg/cm$^2$ (31.25 µl laminin/2 ml ice cold PBS. Stock laminin is from Cultrex 1 mg/ml mouse laminin I (working concentration is 0.05-10 µg/cm$^2$). Thaw the laminin over several hours in fridge. Leave to polymerise in incubator (37° C.) for 4 hours/overnight or longer (overnight seems better particularly for glass bottomed plates.

Dissociate Human ES Cells:

1. Starting hESCs culture should be of good quality, with well-defined, undifferentiated colonies.
   Aspirate the medium from a T25 flask and wash the cells with 3 ml warm Hanks Balanced Solution (Sigma H9394).
   Add 2 ml of warm 0.025% Trypsin-EDTA (Sigma T4174). The stock solution is 0.5%, dilute 1:20 in Hanks (500 µl T/E+9.5 ml Hanks). A fresh working solution should be prepared on the day.
2. Tilt dish to cover the whole surface and incubate for 2-5 min at RT. Not more than 5 min. Collect cell suspension into a 15 ml conical tube containing 4 ml of warm filtered 0.5 mg/ml Soybean Trypsin Inhibitor (Invitrogen, 17075-029) in DMEM (stock is 2 mg/ml). Rinse flask with 2 ml Hanks and add to the tube.
3. Spin at 167×g (1000 rpm in Harrier 18/80) for 5 min.
4. Aspirate the supernatant from the hES cell pellet and very gently re-suspend the cells into 1 ml DFNB media (DMEM/high glucose: F12 mixed 1:1, with N2 and B27 supplements).
5. Pass the cell suspension through a 100 µM cell strainer (BD Falcon). This procedure should yield completely dissociated cells or very small cells aggregates.
6. Collect the filtrate and count cells using Bio-Rad TC20 Automated Cell Counter (dilute 1:2 with Trypan Blue first).
7. Seed 5×10$^3$/cm$^2$ for ONP generation or 9×10$^3$/cm$^2$ for OEP generation, into DFNB media containing 50 ng/ml FGF 3, 50 ng/ml FGF 10, and 10 µM IWR-1-endo (Calbiochem, 681669, stock is 10 mM in DMSO). Maintain cells in this media until end of day 8, fully replacing media every 2 days.
8. Manual purification of cell types of interest can usually occur from day 4-6 of the protocol for ONPs. Sometimes OEP morphology appears later into the protocol (approximately days 7-9).
9. On day 9, remove media and gently wash the cells twice with 2 ml warm DMEM. Replace with DFNB containing 25 ng/ml FGF 3, 25 ng/ml FGF 10, and 2 µM BIO (Sigma, B1686, stock is 2 mM in DMSO). Maintain cells in this media until the end of day 12, fully replacing media every 2 days.

3. Differentiation Potential into Sensory Neurons of Otic Neuroprogenitors Generated by the Standard Fgf Protocol or the Modified Protocol 3

The inventors have compared the ability of otic neural progenitors (ONPs) produced from hES cells using either the FGF protocol (also referred to as the "standard FGF protocol" herein) or the Wnt protocol (also referred to as "modified protocol 3" herein) to differentiate into sensory/auditory neurons.

The protocols used to generate otic progenitors from human embryonic stem (hES) cell were as described previously herein:

DFNB basal media supplemented with FGF3 and FGF10 (50 ng/ml each) for 12 days ("standard FGF protocol" or "FGF protocol")

DFNB basal media supplemented with FGF3 and FGF10 (50 ng/ml each) and 10 µM IWR-1 (Inhibitor of Wnt response-1) for 8 days, followed by FGF3 and FGF10 (25 ng/ml each) and 2 µM BIO (6-bromoindirubin-3'-oxime; GSK-3α/β inhibitor) until day 12 ("Modified Protocol 3", also referred to as the "Wnt protocol").

Otic progenitors induced for 12 days with either method are said to have completed "Phase 1" of the protocol ("phase 1" corresponds to a method of generating otic progenitor cells comprising step (i) and (ii) as defined elsewhere herein). Subsequent neuronal differentiation is referred to as "Phase 2" (where "phase 2" corresponds to method step (iii) as defined elsewhere herein).

ONPs produced from each protocol were tested for their ability to differentiate into more mature neuronal phenotypes, using a standard neuralisation protocol, as described elsewhere herein. Briefly, neuronal differentiation is triggered by dissociating cells with trypsin and plating them at a density of 3-4,000 cells/cm$^2$. Cells are then cultured in high glucose DMEM plus F12 nutrient solution, N2 and B27, supplemented with recombinant human bFGF (20 ng/ml) plus Shh-C24II (500 ng/ml) for three days. On the third day, medium is supplemented with 10 ng ml−1 of BDNF and NT3 and Shh-C24II is removed at the fifth day. Neuralisation was evaluated after 12 days by immunolabelling of characteristic neuronal markers, and gene expression by QPCR analysis.

3.1 Results

Figure 16A:
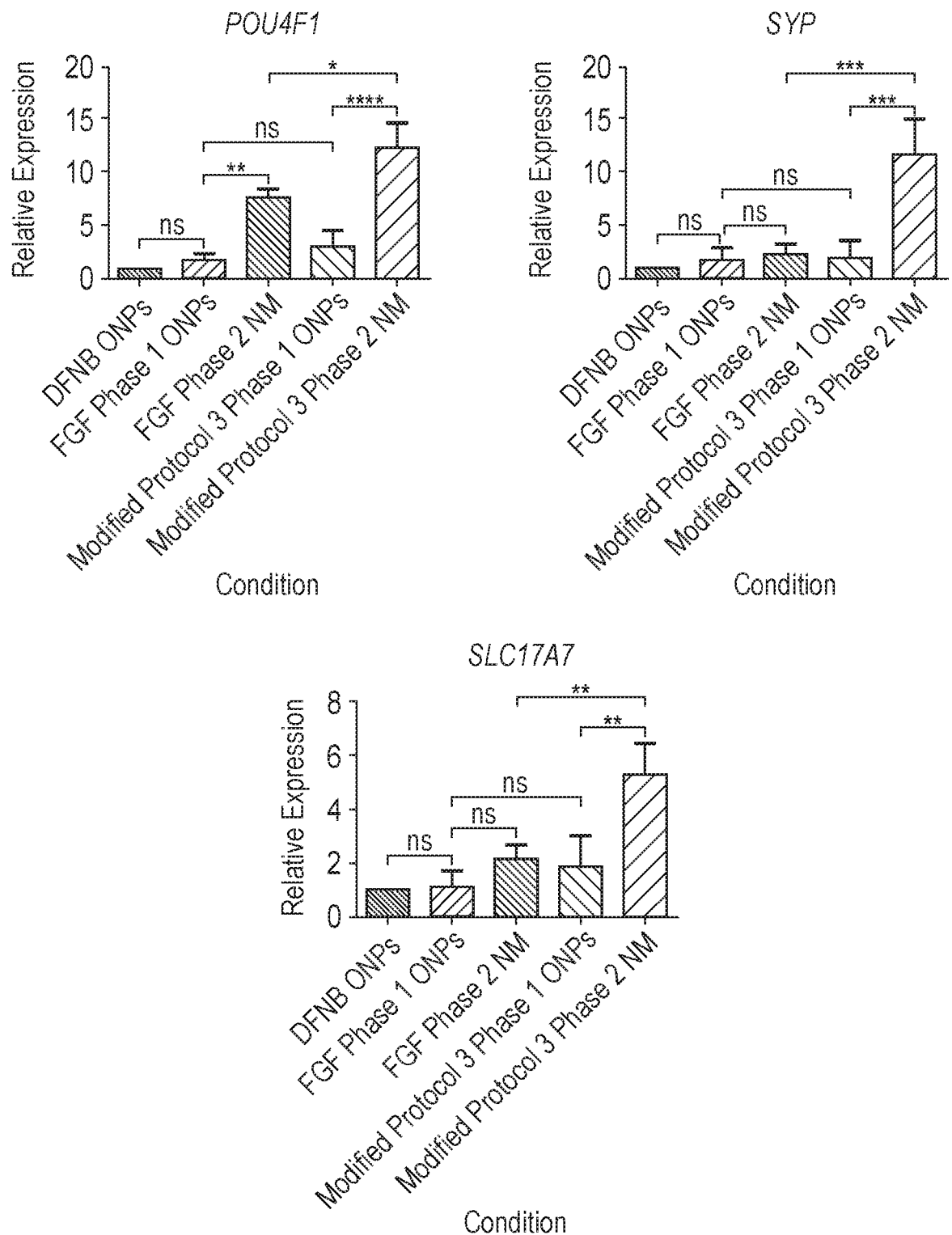
FIG. 16A shows gene expression of sensory neuronal markers POU4F1, SYP and SLC17A7 following a 12 day, Phase 2 neuralisation protocol using H14S9 ONPs. Gene expression is presented as relative to that of baseline DFNB ONPs. Bar charts denote mean and standard deviation of gene expression from n=3 independent experiments. Statistical significance was determined by one way ANOVA with Bonferroni's multiple comparison post-test. ns=no significant difference. *P<0.05, P<0.01, *P<0.001, **P<0.0001.
Figure 16B:
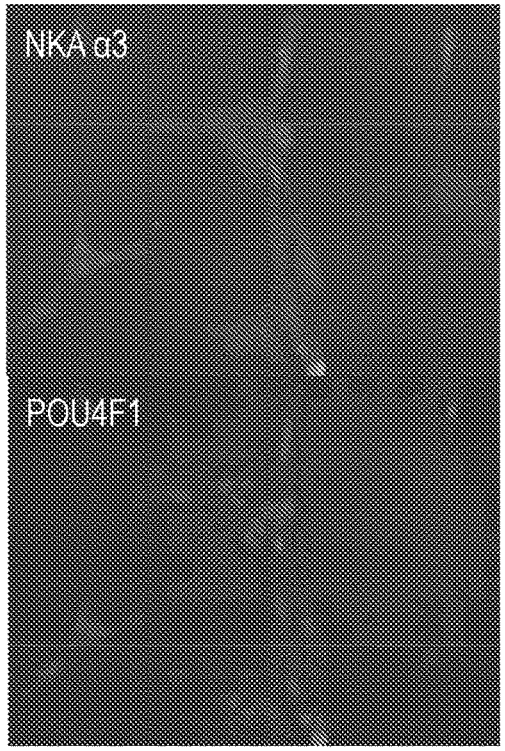
FIG. 16B shows immunolabelling of ONPs (generated from FGF or Wnt Phase 1 protocol) following a 12 day, Phase 2 neuralisation protocol. Cells were labelled with a combination of NKAα3 (green) and POU4F1 (red), or β-tubulin III (green) and NF200 (red). Nuclei counterstained with DAPI. Single representative field of view. Scale bar is 200 μM.
Figure 16B:
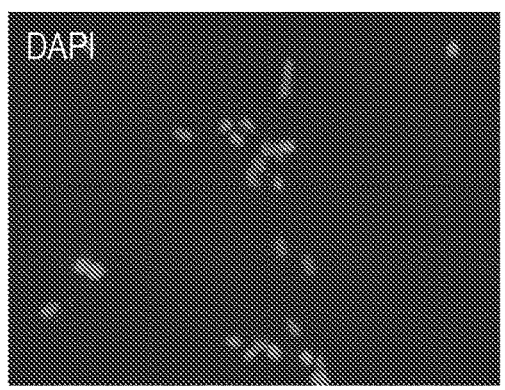
Figure 16B:
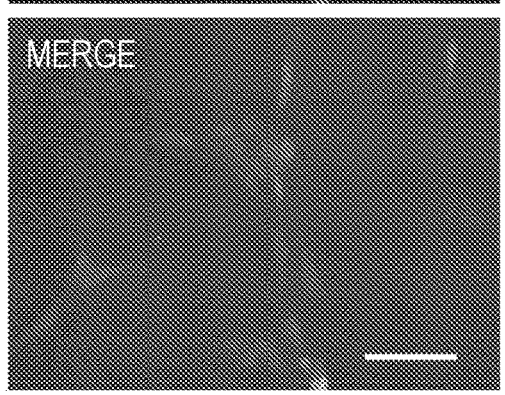
Figure 16B:
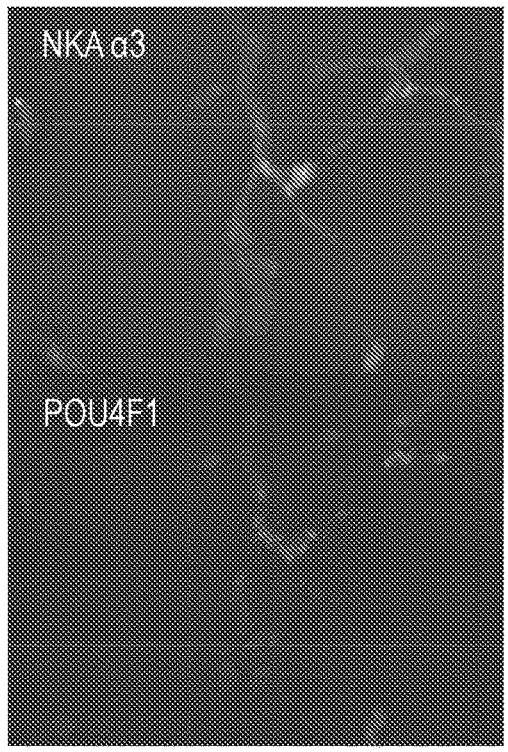
Figure 16B:
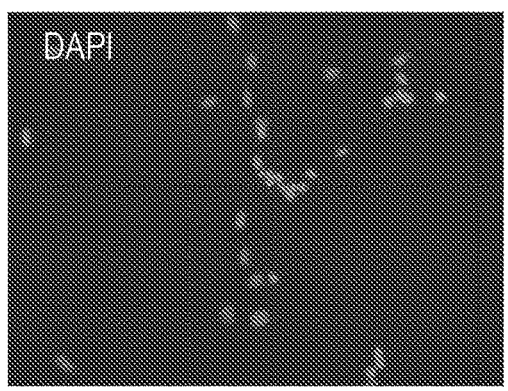
Figure 16B:
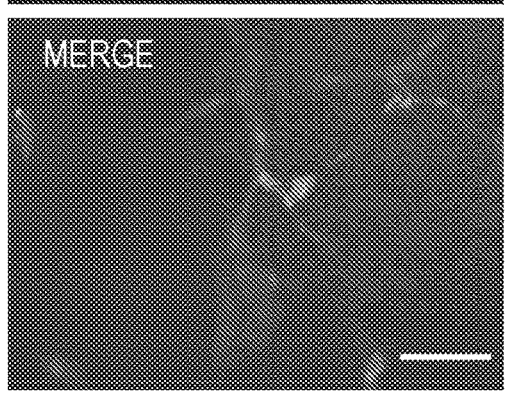
Figure 16B:
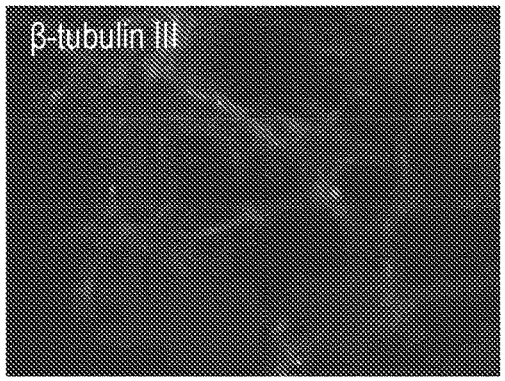
Figure 16B:
Figure 16B:
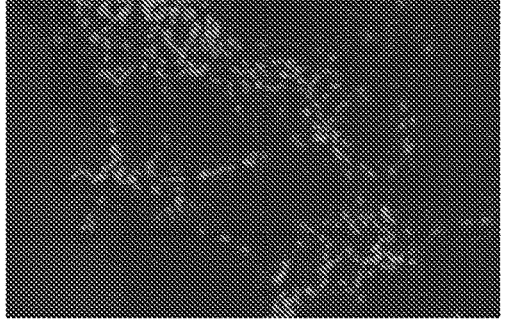
Figure 16B:
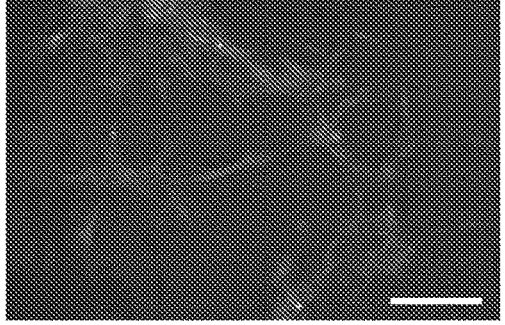
Figure 16B:
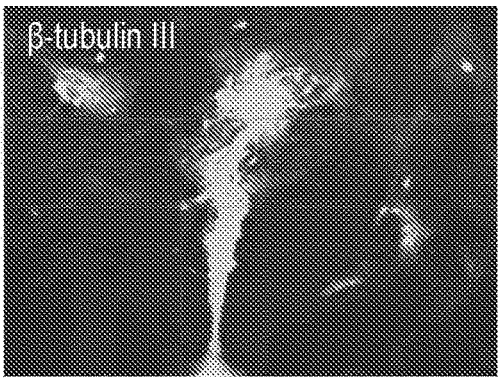
Figure 16B:
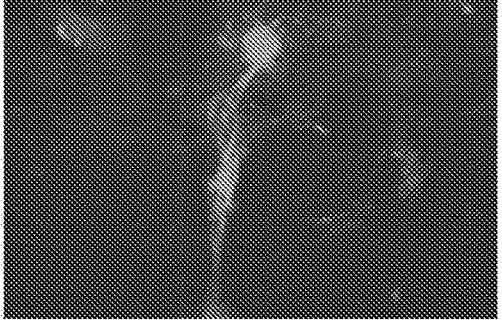
Figure 16B:
Figure 16B:
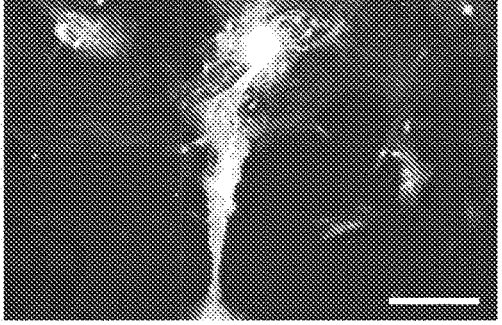
Figure 16C:
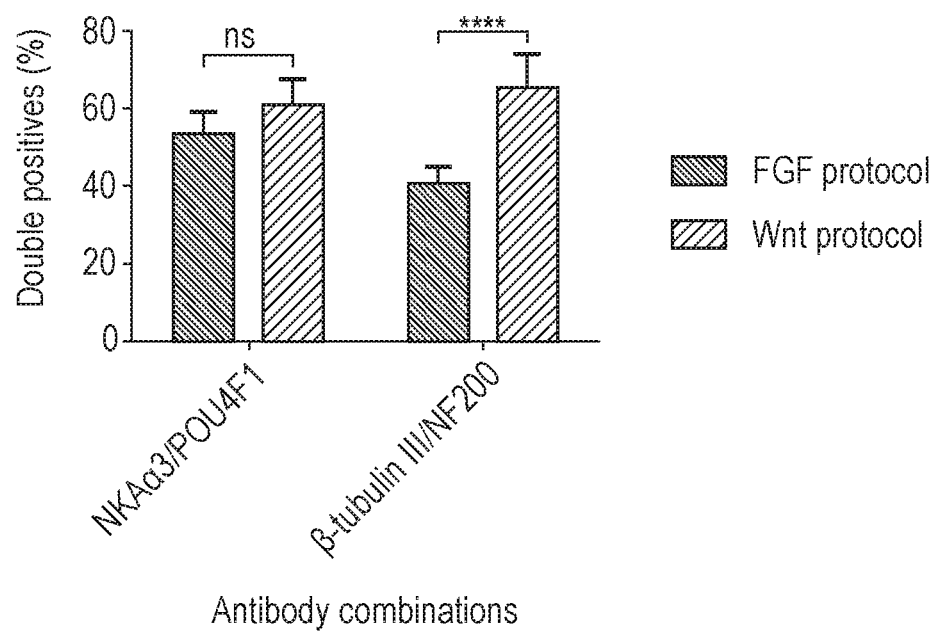
FIG. 16C shows Quantification of neuronal marker immunolabelling. Bar charts show mean percentage of double positive cells labelled with the antibody combinations NKAα3/POU4F1 and β-tubulin III/NF200 from n=3 independent experiments. Error bars denote mean and standard deviation. Statistical significance was determined using Chi-Square with Yates' continuity correction. ns=no significant difference. **P<0.0001.

H14S9 hES cells were differentiated through either the FGF or Wnt protocol for 12 days. Cells were originally seeded at $4 \times 10^3/cm^2$ for the FGF protocol or $6 \times 10^3/cm^2$ for the Wnt protocol. Differentiating cultures were manually cleaned throughout the 12 days to enrich for ONP colonies. At the end of the otic induction, ONP colonies produced from both protocols were subjected to our standard Phase 2 (step iii) neuralisation protocol and differentiated for 12-14 days. QPCR analysis for sensory neuronal markers was carried out for POU4F1/Brn3a, SYP/Synaptophysin, and SLC17A7/VGLUT1 (FIG. 16A), with immunolabelling for NKAα3/POU4F1 and β-tubulin III/NF200 (FIGS. 16B and 16C).

3.2 Discussion

Gene expression of all three sensory neuronal markers investigated (POU4F1, SYP, SLC17A7) was significantly upregulated in the cells generated from the Wnt Phase 1 protocol compared to the standard FGF protocol. There was also a significant upregulation of all three markers between the Wnt protocol progenitors pre- and post-neuralisation. In contrast, using the FGF protocol, only POU4F1 was significantly upregulated after neural differentiation compared to the expression level in the otic progenitor state.

In terms of immunolabelling, there appeared to be no significant difference in the percentage of double positive NKAα3/POU4F1 cells between FGF and Wnt progenitors, although the fluorescence intensity appeared greater in the differentiated Wnt progenitors. However there was a significant increase in the percentage of double positive cells, and fluorescence intensity, for β-tubulin III/NF200 labelling in the Wnt progenitors compared to FGF.

These results suggest that otic progenitors produced using the Wnt protocol have a greater efficiency for further differentiating into the more mature neuronal phenotypes compared to the otic progenitors produced from our standard FGF protocol.

REFERENCES

BLAUWKAMP, T. A., NIGAM, S., ARDEHALI, R., WEISSMAN, I. L. & NUSSE, R. 2012. Endogenous Wnt signalling in human embryonic stem cells generates an equilibrium of distinct lineage-specified progenitors. *Nat Commun*, 3, 1070.

CHEN, B., DODGE, M. E., TANG, W., LU, J., MA, Z., FAN, C. W., WEI, S., HAO, W., KILGORE, J., WILLIAMS, N. S., ROTH, M. G., AMATRUDA, J. F., CHEN, C. & LUM, L. 2009. Small molecule-mediated disruption of Wnt-dependent signaling in tissue regeneration and cancer. *Nat Chem Biol*, 5, 100-7.

CHEN, W., JONGKAMONWIWAT, N., ABBAS, L., ESHTAN, S. J., JOHNSON, S. L., KUHN, S., MILO, M., THURLOW, J. K., ANDREWS, P. W., MARCOTTI, W., MOORE, H. D. & RIVOLTA, M. N. 2012. Restoration of auditory evoked responses by human ES-cell-derived otic progenitors. *Nature*, 490, 278-82.

DINCER, Z, PIAO, J, NIU, GANAT, YKRIKS, S, ZIMMER, SHI, S, TABAR, V & STUDER L 2013. Specification of functional cranial placode derivatives from human pluripotent stem cells. *Cell Reports* 5, 1387-1402

DRAVID, G., YE, Z., HAMMOND, H., CHEN, G., PYLE, A., DONOVAN, P., YU, X. & CHENG, L. 2005. Defining the role of Wnt/beta-catenin signaling in the survival, proliferation, and self-renewal of human embryonic stem cells. *Stem Cells*, 23, 1489-501.

FRETER, S., MUTA, Y., MAK, S. S., RINKWITZ, S. & LADHER, R. K. 2008. Progressive restriction of otic fate: the role of FGF and Wnt in resolving inner ear potential. *Development*, 135, 3415-24.

FREYER, L. & MORROW, B. E. 2010. Canonical Wnt signaling modulates Tbx1, Eya1, and Six1 expression, restricting neurogenesis in the otic vesicle. *Dev Dyn*, 239, 1708-22.

HUDSON, J., TITMARSH, D., HIDALGO, A., WOLVETANG, E. & COOPER-WHITE, J. 2012. Primitive cardiac cells from human embryonic stem cells. *Stem Cells Dev*, 21, 1513-23.

JACQUES, B. E., PULIGILLA, C., WEICHERT, R. M., FERRER-VAQUER, A., HADJANTONAKIS, A. K., KELLEY, M. W. & DABDOUB, A. 2012. A dual function for canonical Wnt/beta-catenin signaling in the developing mammalian cochlea. *Development*, 139, 4395-404.

LEUNG, A W, MOREST, DK, & LI JYH 2013 Differential BMP signaling controls formation and differentiation of multipotent preplacodal ectoderm progenitors from human embryonic stem cells *Dev Biol* 379: 208-220i LIVAK, K. J. & SCHMITTGEN, T. D. 2001. Analysis of relative gene expression data using real-time quantitative PCR and the 2(−Delta Delta C(T)) Method. *Methods*, 25, 402-8.

LOH, K. M., ANG, L. T., ZHANG, J., KUMAR, V., ANG, J., AUYEONG, J. Q., LEE, K. L., CHOO, S. H., LIM, C. Y., NICHANE, M., TAN, J., NOGHABI, M. S., AZZOLA, L., NG, E. S., DURRUTHY-DURRUTHY, J., SEBASTIANO, V., POELLINGER, L., ELEFANTY, A. G., STANLEY, E. G., CHEN, Q., PRABHAKAR, S., WEISSMAN, I. L. & LIM, B. 2014. Efficient endoderm induction from human pluripotent stem cells by logically directing signals controlling lineage bifurcations. *Cell Stem Cell*, 14, 237-52.

MEIJER, L., SKALTSOUNIS, A. L., MAGIATIS, P., POLYCHRONOPOULOS, P., KNOCKAERT, M., LEOST, M., RYAN, X. P., VONICA, C. A., BRIVANLOU, A., DAJANI, R., CROVACE, C., TARRICONE, C., MUSACCHIO, A., ROE, S. M., PEARL, L. & GREENGARD, P. 2003. GSK-3-selective inhibitors derived from Tyrian purple indirubins. *Chem Biol*, 10, 1255-66.

OHYAMA, T., MOHAMED, 0. A., TAKETO, M. M., DUFORT, D. & GROVES, A. K. 2006. Wnt signals mediate a fate decision between otic placode and epidermis. *Development*, 133, 865-75.

RONAGHI, M., NASR, M., EALY, M., DURRUTHY-DURRUTHY, R., WALDHAUS, J., DIAZ, G. H., JOUBERT, L. M., OSHIMA, K. & HELLER, S. 2014. Inner ear hair cell-like cells from human embryonic stem cells. *Stem Cells Dev*, 23, 1275-84.

SHI, F, CORRALES E, LIBERMAN MC & EDGE A S. BMP4 induction of sensory neurons from hESCs and innervation of sensory epithelium. 2007 *European Journal of Neuroscience*, Vol. 26, pp. 3016-3023

SOKOL, S. Y. 2011. Maintaining embryonic stem cell pluripotency with Wnt signaling. *Development*, 138, 4341-50.

TSENG, A. S., ENGEL, F. B. & KEATING, M. T. 2006. The GSK-3 inhibitor BIO promotes proliferation in mammalian cardiomyocytes. *Chem Biol*, 13, 957-63.

VENDRELL, V., VAZQUEZ-ECHEVERRIA, C., LOPEZ-HERNANDEZ, I., ALONSO, B. D., MARTINEZ, S., PUJADES, C. & SCHIMMANG, T. 2013. Roles of Wnt8a during formation and patterning of the mouse inner ear. *Mech Dev*, 130, 160-8.

The invention claimed is:

1. A method of generating otic progenitor cells comprising the sequential steps of:
   i) culturing a progenitor cell under conditions sufficient to inhibit Wnt signalling and activate FGF signalling for a first time period sufficient to induce upregulation of one or more otic cell markers; and
   ii) culturing the progenitor cell of step i) under conditions sufficient to activate Wnt signalling and reduce but not completely abolish FGF signalling relative to step i) for a second time period sufficient to maintain upregulated expression of said one or more otic cell markers, wherein the conditions of step (i) comprise supplementation with first one or more FGFs at a concentration of 1-100 ng/ml each, and wherein the conditions of step (ii) comprise supplementation of second one or more FGFs at a total concentration of less than or equal to 80% of total FGF concentration used in step (i).

2. The method of claim 1, wherein said progenitor cell is a pluripotent stem cell.

3. The method of claim 2, wherein said pluripotent stem cell is an embryonic stem cell or an induced pluripotent stem cell.

4. The method of claim 1, wherein said otic progenitor cells comprise one or more otic epithelial progenitor cells and/or one or more otic neural progenitor cells.

5. The method of claim 1, wherein said one or more otic cell markers are one or more of PAX2, PAX8, FOXG1 and SOX2.

6. The method of claim 1, wherein said upregulation of one or more otic cell markers is determined by measuring mRNA and/or protein levels.

7. The method of claim 1, wherein said conditions sufficient to inhibit Wnt signalling further comprise culturing said progenitor cell in a culture medium comprising one or more Wnt inhibitors.

8. The method of claim 7, wherein said one or more Wnt inhibitors is IWR-1-endo.

9. The method of claim 1, wherein the first one or more FGFs and the second one or more FGFs are one or two FGFs.

10. The method of claim 9, wherein concentration of each the second one or more FGFs is up to 30 ng/ml.

11. The method of claim 10, wherein the first one or more FGFs are same as the second one or more FGFs.

12. The method of claim 1, wherein the first one or more FGFs and the second one or more FGFs are one or both of FGF3 and FGF10.

13. The method of claim 1, wherein said progenitor cell is cultured as a monolayer.

14. The method of claim 1, wherein said progenitor cell is cultured in serum free conditions.

15. The method of claim 1, wherein inhibition of Wnt signalling occurs prior to otic progenitor cell differentiation.

16. The method of claim 1, wherein said first time period is at least 24, 48, 72, 96, 120, 144, 168, 192, 216, 240, 264 or 288 hours.

17. The method of claim 1, wherein said second time period is at least 24, 48, 72, 96, 120, 144, 168, or 192 hours.

18. The method of claim 1, wherein the method further comprises a step iii) comprising differentiating said otic progenitor cells into hair-cell-like cells; or a step iv) comprising differentiating said otic progenitor cells into auditory or sensory neurons.

19. The method of claim 9, wherein concentration of each the second one or more FGFs is 5-30 ng/ml.

* * * * *